(12) United States Patent
Jaeschke et al.

(10) Patent No.: US 8,334,287 B2
(45) Date of Patent: Dec. 18, 2012

(54) IMIDAZOLES

(75) Inventors: Georg Jaeschke, Basel (CH); Lothar Lindemann, Basel (CH); Eric Vieira, Frenkendorf (CH); Juergen Wichmann, Steinen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 13 days.

(21) Appl. No.: 12/833,017

(22) Filed: Jul. 9, 2010

(65) Prior Publication Data

US 2011/0015202 A1   Jan. 20, 2011

(30) Foreign Application Priority Data

Jul. 17, 2009   (EP) ..................... 09165780

(51) Int. Cl.
*A61K 31/4965* (2006.01)
*C07D 401/04* (2006.01)

(52) U.S. Cl. ............. 514/252.03; 514/341; 514/333; 546/274.1; 544/405; 544/319

(58) Field of Classification Search ............. 514/252.03, 514/341, 333; 546/274.1; 544/405, 319
See application file for complete search history.

(56) References Cited

U.S. PATENT DOCUMENTS

| 7,153,874 | B2 * | 12/2006 | Buettelmann et al. | 514/341 |
| 7,241,760 | B2 * | 7/2007 | Buettelmann et al. | 514/235.8 |
| 7,332,510 | B2 * | 2/2008 | Buettelmann et al. | 514/341 |
| 2005/0054686 | A1 | 3/2005 | Buettelmann et al. | |
| 2006/0030559 | A1 * | 2/2006 | Buettelmann et al. | 514/227.8 |
| 2008/0103306 | A1 * | 5/2008 | Buettelmann et al. | 544/333 |

FOREIGN PATENT DOCUMENTS

| WO | 02/46166 | 6/2002 |
| WO | 03/047581 | 6/2003 |
| WO | 2004080998 | 9/2004 |
| WO | 2005118568 | 12/2005 |
| WO | 2008066750 | 6/2008 |

OTHER PUBLICATIONS

Schlaeger et al., Cytotechnology 30:71-83 ( 1999).
(Translation of Israeli Off Act in Corres Israeli App 261746 Feb. 29, 2012).
Mutel et al., Expert Opinion on Therapeutic Patents (2002) vol. 12, No. 12, pp. 1845-1852.
Shinohe et al., Progress in Neuro-Psychopharmacology & Biological Psychiatry vol. 32, p. 911 (2008).
Jaeschke et al , Expert Opinion on Therapeutic Patents (2008) vol. 18 No. 2, p. 123-142.
Porter et al., British Journal of Pharmacology (1999) vol. 128, p. 13-20.
International Search Report issued Aug. 12, 2010, in corresponding Internation Application PCT/EP2010/060097 filed Jul. 14, 2010.
Movsesyan, V. et al., J. Pharmacol. Exp. Ther. 296(11):47-47 ( 2001).
Anderson, J. et al., Eur. J. Pharmacol. 473(1):35-40 ( 2003).
(Opposition by Alafar to Corres. Ecuadorean Appl. SP1211611-PCT Sep. 15, 2012).

* cited by examiner

*Primary Examiner* — Rei-tsang Shiao
(74) *Attorney, Agent, or Firm* — George W. Johnston; Patricia S. Rocha-Tramaloni; Kimberly J. Prior

(57) ABSTRACT

The present invention relates to imidazole derivatives of the general formula

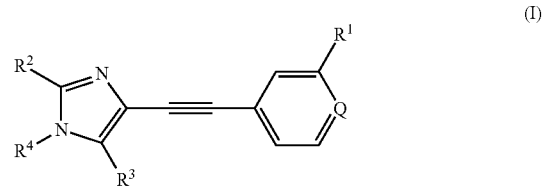

(I)

wherein $R^1$, $R^2$, $R^3$, and $R^4$ are as defined in the specification and to pharmaceutically acceptable salts thereof. Compounds of formula I are metabotropic glutamate receptor antagonists. They can be used in the treatment or prevention of mGluR5 receptor mediated disorders.

21 Claims, No Drawings

IMIDAZOLES

PRIORITY TO RELATED APPLICATION(S)

This application claims the benefit of European Patent Application No. 09165780.9, filed Jul. 17, 2009, which is hereby incorporated by reference in its entirety.

BACKGROUND OF THE INVENTION

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups:
mGluR1 and mGluR5 belong to group I,
mGluR2 and mGluR3 belong to group II, and
mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, L-dopa induced dyskinesia, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)). Furthermore, *Expert Opin. Ther. Patents* (2008), 18(2) describes the treatment of mGluR5 antagonists in situations where mGluR5 activity is exacerbated due to a specific genetic background such as Fragile-X syndrome. Fragile X patients suffer from cognitive impairment, autism spectrum disorder, aggression, seizure, anxiety, obsessive compulsive disorder, excessive tactile sensitivity, loose bowel and sensory hyper-excitability. Described in this document is also the benefit in the treatment of addiction (drugs, opioids, nicotine and alcohol), gastro-esophageal acid reflux disease (GERD), cancer and overactive bladder.

MGluR5 antagonists play also a role in situations where elevated glutamate tonus is present, for example in autism (*Progress in Neuro-Psychopharmacology & Biological Psychiatry*, 32, 2008, 911 and WO2008/066750).

Selective mGluR5 antagonists are especially useful for the treatment of fragile-X, depression, Parkinson and L-dopa induced dyskinesia.

SUMMARY OF THE INVENTION

The present invention provides imidazoles of formula I

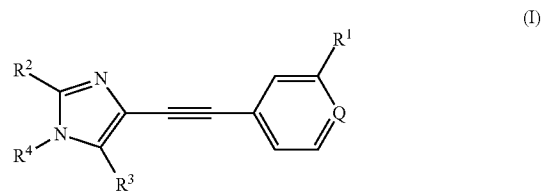

wherein
$R^1$ is halogen, lower alkyl or lower alkoxy;
$R^2$ is lower alkyl, lower hydroxyalkyl or lower alkoxyalkyl;
$R^3$ is hydrogen, lower alkyl, lower hydroxyalkyl or lower alkoxyalkyl;
Q is either —N= or —CH=;
$R^4$ is a group of formula IIa or IIb

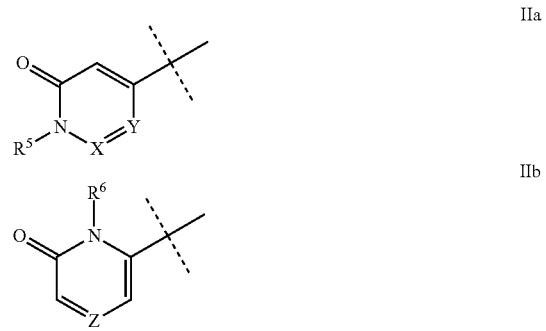

wherein
X, Y and Z are each independently —CH= or —N=, and whereby only one of X or Y is a nitrogen atom;
$R^5$ and $R^6$ are each independently hydrogen, lower alkyl, lower hydroxyalkyl, lower alkoxyalkyl, —$(CH_2)_m$—(CO)O-lower alkyl, —$(CH_2)_m$—$S(O)_2$-lower alkyl, —$(CH_2)_m$—C(O)—NR'R" and
where m=0-3 and R' and R" are each independently hydrogen or lower alkyl;
and pharmaceutically acceptable salts thereof.

Compounds of formula I are metabotropic glutamate receptor antagonists. Compounds of formula I are distinguished by having valuable therapeutic properties. They can be used in the treatment or prevention of mGluR5 receptor mediated disorders.

The invention provides compounds of formula I, their pharmaceutically acceptable salts, and the above-mentioned compounds as pharmaceutically active substances and their production.

The invention also provides a process for preparing a compound according to formula I following the general procedures as outlined below for compounds of formula I.

Moreover the invention also provides medicaments containing one or more compounds of the present invention and pharmaceutically acceptable excipients for the treatment and prevention of mGluR5 receptor mediated disorders, such as acute and/or chronic neurological disorders, in particular Alzheimer's disease, senile dementia, Parkinson's disease, L-dopa induced dyskinesia, Huntington's chorea, amyotrophic lateral sclerosis and multiple sclerosis, schizophrenia, anxiety, depression, pain, drug dependency, fragile-X syndrome, autism, addiction (drugs, opioids, nicotine and alcohol), gastro-esophageal acid reflux disease (GERD), cancer and overactive bladder.

The invention also provides the use of a compound in accordance with the present invention as well as its pharmaceutically acceptable salt for the manufacture of medicaments for the treatment and prevention of mGluR5 receptor mediated disorders as outlined above.

The following definitions of general terms used in the present description apply irrespective of whether the terms in question appear alone or in combination.

DETAILED DESCRIPTION OF THE INVENTION

The term "lower alkyl" used in the present description denotes straight-chain or branched saturated hydrocarbon residues with 1 to 6 carbon atoms, in particular with 1 to 4 carbon atoms, such as methyl, ethyl, n-propyl, i-propyl, n-butyl, t-butyl and the like.

The term "lower alkoxy" denotes an —O—$C_{1-6}$ alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers.

The term "lower alkoxyalkyl" denotes a lower alkoxy group as defined above, wherein the O-atom is further bonded to a lower alkyl group.

The term "lower hydroxyalkyl" denotes a lower alkyl group as defined above, wherein at least one hydrogen atom is replaced by a hydroxy group.

The term "halogen" denotes fluorine, chlorine, bromine and iodine.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salt" refers to any salt derived from an inorganic or organic acid or base.

"Therapeutically effective amount" means an amount that is effective to prevent, alleviate or ameliorate symptoms of disease or prolong the survival of the subject being treated.

Encompassed by the instant invention are also all tautomeric forms of compounds of formula I, for example for $R^4$, if $R^5$ and $R^6$ are hydrogen:

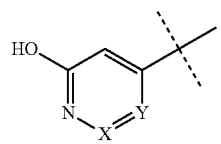

IIa

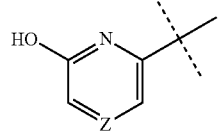

IIb

The compounds of formula I comprise the following substructures:

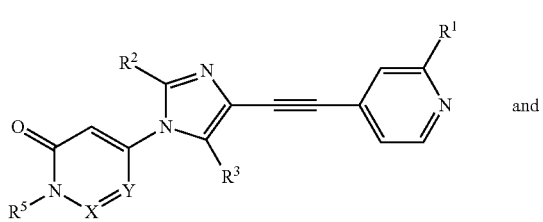

IA and

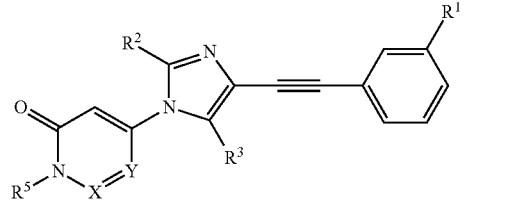

IB

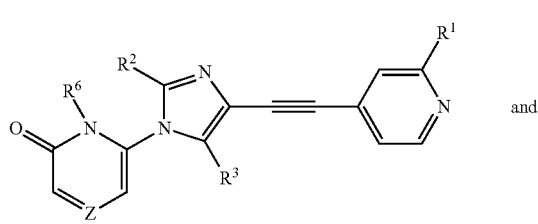

IC and

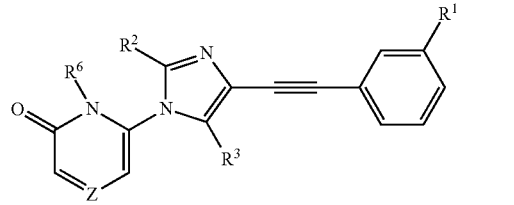

ID wherein
$R^1$ is halogen, lower alkyl or lower alkoxy;
$R^2$ is lower alkyl, lower hydroxyalkyl or lower alkoxyalkyl;
$R^3$ is hydrogen, lower alkyl, lower hydroxyalkyl or lower alkoxyalkyl;
X, Y and Z are each independently —CH═ or —N═, and whereby only one of X or Y is a nitrogen atom;
$R^5$ and $R^6$ are each independently hydrogen, lower alkyl, lower hydroxyalkyl, lower alkoxyalkyl, —(CH$_2$)$_m$—(CO) O-lower alkyl, —(CH$_2$)$_m$—S(O)$_2$-lower alkyl, —(CH$_2$)$_m$—C(O)—NR'R" and
where m=0-3 and R' and R" are each independently hydrogen or lower alkyl;
as well as pharmaceutically acceptable salts thereof.

An embodiment of the invention are compounds of formula IA, wherein X and Y are —CH═ and $R^1$ is halogen, for example the following compounds:

4-[4-(2-chloro-pyridin-4-ylethynyl)-2-methyl-imidazol-1-yl]-1H-pyridin-2-one
4-[4-(2-chloro-pyridin-4-ylethynyl)-2-methyl-imidazol-1-yl]-1-methyl-1H-pyridin-2-one and
4-[4-(2-chloro-pyridin-4-ylethynyl)-2,5-dimethyl-imidazol-1-yl]-1-methyl-1H-pyridin-2-one.

A further embodiment are compounds of formula IB, wherein X and Y are —CH═ and $R^1$ is halogen, for example the following compounds:
4-[4-(3-chloro-phenylethynyl)-2-methyl-imidazol-1-yl]-1H-pyridin-2-one
4-[4-(3-chloro-phenylethynyl)-2-methyl-imidazol-1-yl]-1-methyl-1H-pyridin-2-one
4-[4-(3-chloro-phenylethynyl)-2-methyl-imidazol-1-yl]-1-ethyl-1H-pyridin-2-one
4-[4-(3-chloro-phenylethynyl)-2-methyl-imidazol-1-yl]-1-(2-methoxy-ethyl)-1H-pyridin-2-one
4-[4-(3-chloro-phenylethynyl)-2,5-dimethyl-imidazol-1-yl]-1H-pyridin-2-one
4-[4-(3-chloro-phenylethynyl)-2,5-dimethyl-imidazol-1-yl]-1-methyl-1H-pyridin-2-one
4-[4-(3-chloro-phenylethynyl)-2,5-dimethyl-imidazol-1-yl]-1-ethyl-1H-pyridin-2-one
4-[4-(3-chloro-phenylethynyl)-2,5-dimethyl-imidazol-1-yl]-1-(2-methoxy-ethyl)-1H-pyridin-2-one and
4-[4-(3-fluoro-phenylethynyl)-2,5-dimethyl-imidazol-1-yl]-1-methyl-1H-pyridin-2-one.

A further embodiment are compounds of formula IB, wherein X and Y are —CH═ and $R^1$ is lower alkyl, for example the following compounds:
4-(2-methyl-4-m-tolylethynyl-imidazol-1-yl)-1H-pyridin-2-one
1-methyl-4-(2-methyl-4-m-tolylethynyl-imidazol-1-yl)-1H-pyridin-2-one
1-ethyl-4-(2-methyl-4-m-tolylethynyl-imidazol-1-yl)-1H-pyridin-2-one
1-(2-methoxy-ethyl)-4-(2-methyl-4-m-tolylethynyl-imidazol-1-yl)-1H-pyridin-2-one
[4-(2-methyl-4-m-tolylethynyl-imidazol-1-yl)-2-oxo-2H-pyridin-1-yl]-acetic acid ethyl ester
4-[2,5-dimethyl-4-m-tolylethynyl-imidazol-1-yl]-1-methyl-1H-pyridin-2-one
4-[2,5-dimethyl-4-m-tolylethynyl-imidazol-1-yl]-1-ethyl-1H-pyridin-2-one and
4-[2,5-dimethyl-4-m-tolylethynyl-imidazol-1-yl]-1-(2-methoxy-ethyl)-1H-pyridin-2-one.

A further embodiment are compounds of formula IB, wherein X is —N═ and Y is —CH═ and $R^1$ is halogen, for example the following compounds:
5-[4-(3-chloro-phenylethynyl)-2-methyl-imidazol-1-yl]-2-methyl-2H-pyridazin-3-one
5-[4-(3-chloro-phenylethynyl)-2,5-dimethyl-imidazol-1-yl]-2-methyl-2H-pyridazin-3-one
5-[4-(3-Chloro-phenylethynyl)-2-methyl-imidazol-1-yl]-2-ethyl-2H-pyridazin-3-one and
5-[4-(3-chloro-phenylethynyl)-2-methyl-imidazol-1-yl]-2-(2-methoxy-ethyl)-2H-pyridazin-3-one.

A further embodiment are compounds of formula IB, wherein X is —N═ and Y is —CH═ and $R^1$ is lower alkyl, for example the following compounds:
2-Methyl-5-(2-methyl-4-m-tolylethynyl-imidazol-1-yl)-2H-pyridazin-3-one
5-(2,5-dimethyl-4-m-tolylethynyl-imidazol-1-yl)-2-methyl-2H-pyridazin-3-one
2-ethyl-5-(2-methyl-4-m-tolylethynyl-imidazol-1-yl)-2H-pyridazin-3-one and
2-(2-methoxy-ethyl)-5-(2-methyl-4-m-tolylethynyl-imidazol-1-yl)-2H-pyridazin-3-one.

A further embodiment are compounds of formula IB, wherein X is —CH═ and Y is —N═ and $R^1$ is lower alkyl, for example the following compound:
6-(2,5-dimethyl-4-m-tolylethynyl-imidazol-1-yl)-3-methyl-3H-pyrimidin-4-one.

A further embodiment are compounds of formula IC, wherein Z is —CH═ and $R^1$ is halogen, for example the following compound:
6-[4-(2-chloro-pyridin-4-ylethynyl)-2-methyl-imidazol-1-yl]-pyridin-2-ol.

A further embodiment are compounds of formula ID, wherein Z is —CH═ and $R^1$ is halogen, for example the following compounds:
6-[4-(3-chloro-phenylethynyl)-2-methyl-imidazol-1-yl]-pyridin-2-ol and
6-[4-(3-chloro-phenylethynyl)-2-methyl-imidazol-1-yl]-1-methyl-1H-pyridin-2-one.

The compounds of formula I of the invention may be prepared according to a process which comprises:
(a) reacting a compound of formula IV

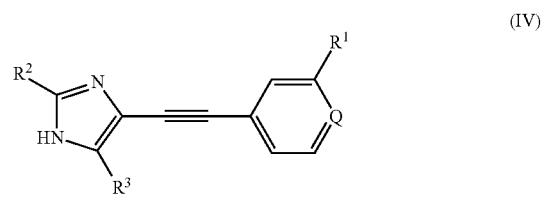

(IV)

wherein $R^1$, $R^2$, $R^3$ and Q have the meanings as defined above, with a protected compound of formula

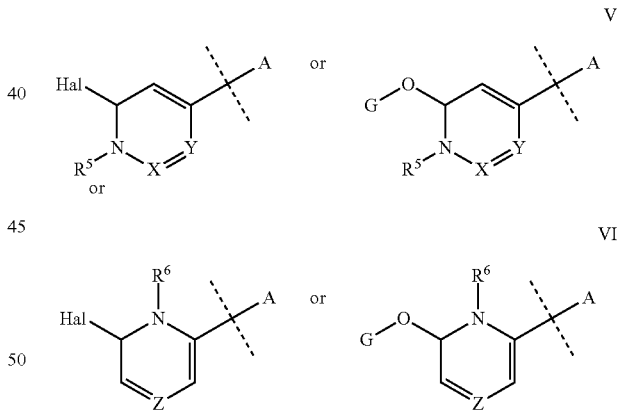

V

VI wherein A is halogen or trifluoromethanesulfonyloxy ($OSO_2CF_3$), trimethylstannyl, tributylstannyl, or —B(OR$^a$)$_2$ where $R^a$ can either be hydrogen, lower alkyl or both $R^a$ groups can be linked together to form a 5-6 membered (dioxolane or dioxane) ring, G is hydrogen or a suitable O-protecting group such as trimethylsilyoxymethyl (SEM) or methoxymethyl (MOM) or allyl or the like, Hal is, for example, chlorine or fluorine which can be transformed to a GO-group by known procedures (eg. hydrolys, alcoholysis and the like), G is hydrogen or a suitable N-protecting group such as tert-Butyloxycarbonyl (Boc), a pyrrole ring (e.g. 2,5-dimethylpyrrole), benzyl, benzoyl, acetyl, phthalimido or the like, and deprotecting the obtained compounds or (b) reacting a compound of formula VII

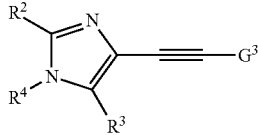

wherein $R^2$, $R^3$ and $R^4$ have the meanings as defined above, and $G^3$ is hydrogen or trialkylsilyl- with a compound of formula VIII

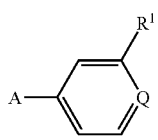

wherein $R^1$ A and Q have the meanings as defined above, or (c) reacting a compound of formula IX

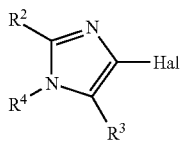

wherein $R^2$, $R^3$ and $R^4$ have the meanings as defined above and Hal is halogen, in particular bromine or iodine with a compound of formula X

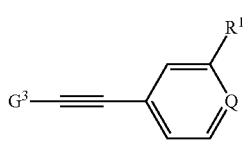

wherein $R^1$, $G^3$ and Q have the meanings as defined above and if desired, converting the compounds obtained into pharmaceutically acceptable acid addition salts.

Furthermore, compounds of formula IX

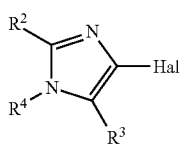

wherein $R^2$, $R^3$ and $R^4$ have the meanings as defined above and Hal is halogen, can be synthesized by the following procedures:

i) by reaction of a compound of V or VI with a compound of formula X to form a compound of formula XI

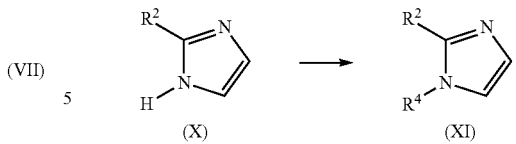

Compound XI is then transformed via halogenation to a compound of Formula XII which can be selectively transformed into a compound of formula IX:

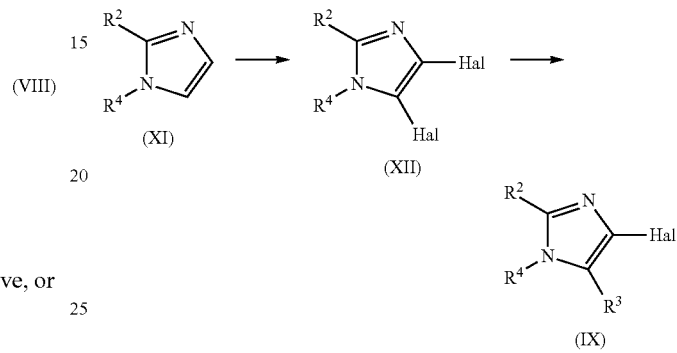

ii) Using another procedure, a compound of formula V can be directly transformed into a compound of formula IX by reaction with a compound of formula XIV where A is halogen, for example, fluorine or chlorine.

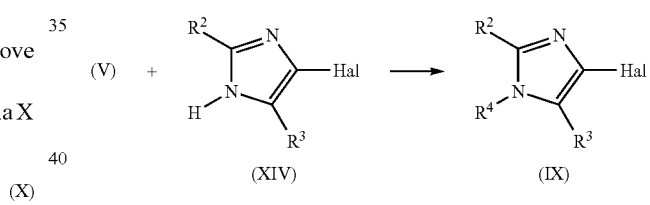

iii) Finally, compounds of Formula I can also be obtained by alkylation of any of the above intermediates where $R^5$, $R^6$ or $R^7$ is hydrogen with alkylating agents (alkyl halides, alkyl triflates, dialkylsulfates and the like) to obtain compounds of formula I where $R^5$, $R^6$ or $R^7$ are not hydrogen.

Pharmaceutically acceptable salts of compounds of formula I can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formula I and their pharmaceutically acceptable salts are, as already mentioned above, metabotropic glutamate receptor antagonists and can be used for the treatment or prevention of mGluR5 receptor mediated disorders, such as acute and/or chronic neurological disorders, cognitive disorders and memory deficits, as well as acute and chronic pain. Treatable neurological disorders are for instance Alzheimer's disease, senile dementia, Parkinson's disease, L-dopa induced dyskinesia, Huntington's chorea, amyotrophic lateral sclerosis and multiple sclerosis, schizophrenia, anxiety, depression, pain, drug dependency, fragile-X syndrome, autism, addiction (drugs, opioids, nicotine and alcohol), gastro-esophageal acid reflux disease (GERD), cancer and overactive.

The compounds of formula I and their pharmaceutically acceptable salts are especially useful in the treatment of fragile-X, depression, Parkinson and L-dopa induced dyskinesia.

The pharmacological activity of the compounds was tested using the following method:

For binding experiments, cDNA encoding human mGlu5a receptor was transiently transfected into EBNA cells using a procedure described by E.-J. Schlaeger and K. Christensen (*Cytotechnology* 1998, 15, 1-13). For functional assays, $[Ca^{2+}]i$ measurements were performed largely as described previously (Porter et al., Br J. Pharmacol 1999, 128, 13-20) on stably expressed recombinant human mGlu 5a receptors in HEK-293 cells. The cells were dye loaded using Fluo 4-AM (purchased from Molecular Probes, 2 μM final concentration) $[Ca^{2+}]i$ measurements were performed using a fluorometric imaging plate reader (FLIPR, Molecular Devices Corporation, La Jolla, Calif., USA). Antagonist evaluation was performed following a 5 minute preincubation with the test compounds followed by the addition of a submaximal addition of agonist.

The inhibition (antagonists) curves were fitted with a four parameter logistic equation giving $IC_{50}$, and Hill coefficient using the iterative non linear curve fitting software Xcel fit.

The Ki values of the compounds tested are given. The Ki value is defined by the following formula:

$$K_i = IC_{50}/1 + L/K_d$$

in which the $IC_{50}$ values are those concentrations of the compounds tested in which causes 50% inhibition of the competing radioligand ($[^3H]$MPEP). [L] is the concentration of radioligand used in the binding experiment and the $K_d$ value of the radioligand is empiracally determined for each batch of membranes prepared.

The compounds of the present invention are mGluR5a receptor antagonists. The activities of compounds of formula I as measured in the assay described above are in the range of $K_i$<1000 nM.

| Example No./Formula | Ki (nM) | Example No./Formula | Ki (nM) |
|---|---|---|---|
| 1/IB | 40 | 29/IB | 58 |
| 2/IB | 69 | 30/IB | 211 |
| 3/IB | 39 | 31/IB | 61 |
| 4/IB | 345 | 32/IB | 46 |
| 5/IB | 44 | 33/IB | 446 |
| 6/IA | 146 | 34/IB | 87 |
| 7/IA | 180 | 35/IA | 347 |
| 8/IB | 113 | 36/IA | 173 |
| 9/IB | 42 | 37/IA | 238 |
| 10/IB | 75 | 39/IA | 285 |

-continued

| Example No./Formula | Ki (nM) | Example No./Formula | Ki (nM) |
|---|---|---|---|
| 11/IB | 265 | 41/IB | 52 |
| 12/IB | 40 | 42/IB | 38 |
| 13/IB | 94 | 43/IA | 306 |
| 14/ID | 42 | 44/IB | 71 |
| 15/ID | 154 | 45/IB | 74 |
| 16/ID | 659 | 46/IA | 569 |
| 17/IC | 144 | 48/IB | 788 |
| 18/IC | 559 | 50/IB | 559 |
| 19/IC | 504 | 51/IB | 53 |
| 20/IC | 817 | 52/IB | 37 |
| 21/IB | 40 | 53/IA | 204 |
| 22/IA | 384 | 54/IB | 131 |
| 23/IB | 52 | 55/IB | 93 |
| 24/IA | 277 | 56/IA | 597 |
| 25/IB | 148 | 57/IA | 808 |
| 26/IB | 33 | | |
| 27/IB | 40 | | |
| 28/IB | 222 | | |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, in particular between 7 and 700 mg per day.

The following examples are provided to further elucidate the invention:

EXAMPLE 1

4-[4-(3-chloro-phenylethynyl)-2-methyl-imidazol-1-yl]-1H-pyridin-2-one

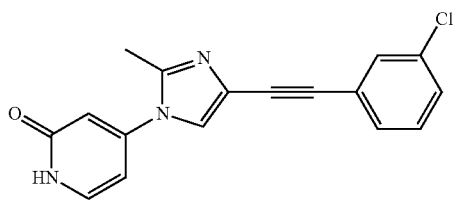

a) 2-chloro-4-[4-(3-chloro-phenylethynyl)-2-methyl-imidazol-1-yl]-pyridine (120 mg, 0.366 mmol) was dissolved in 6 ml tert-butanol. A 50% solution of KOH (2 ml, 26.7 mmol) was added and the mixture was refluxed for 72 h. The reaction mixture was concentrated in vaccuo, the pH was adjusted to 7 by addition of 37% HCl solution, and the aqueous phase was extracted twice with 40 ml of ethyl acetate. The organic phase was washed once with 10 of brine, dried with magnesium sulfate, filtered and evaporated. The title compound (104 mg, 0.336 mmol, 92%) was obtained as a crystalline light yellow solid, MS: m/e=310.1, 312.2 (M+H$^+$).

b) 2-chloro-4-[4-(3-chloro-phenylethynyl)-2-methyl-imidazol-1-yl]-pyridine

To a solution of 400 mg (1.85 mmol) of 4-(3-chloro-phenylethynyl)-2-methyl-1H-imidazole and 1.12 ml (1.46 g, 11.1 mmol) of 2-chloro-4-fluoropyridine in 5 ml of DMF were added 1.2 g (3.69 mmol) of cesium carbonate. The mixture was heated to 100° C. for 4 h, allowed to cool and concentrated in vaccuo. The residue was taken up in 20 ml ethyl acetate and the organic phase was washed twice with 20 ml of water and dried over magnesium sulfate. After treatment with charcoal, the solution was filtered and concentrated to yield 531 mg (1.62 mmol, 88%) of the title compound as an off-white crystalline solid, MS: m/e=328.1, 330.1 (M+H$^+$).

c) 4-(3-chloro-phenylethynyl)-2-methyl-1H-imidazole

To a solution of 500 mg (2.40 mmol) of 5-iodo-2-methyl-1H-imidazole (CAS: [73746-45-9]) in 7 ml of DMF were added under an argon atmosphere 118 mg (0.17 mmol) of Bis(triphenylphosphine)palladium dichloride and 0.67 ml (4.81 mmol) of triethylamine. The mixture was stirred for 10 min at room temperature. Then 0.52 ml (575 mg, 4.09 mmol) of 3-chloro-1-ethynyl-benzene and 13.7 mg (0.072 mmol) of copper(I) iodide were added and the mixture was stirred for 1.5 h at 60° C. The mixture was concentrated in vaccuo, dissolved in a minimal volume of methylene chloride and purified by chromatography on 20 g of silicagel (gradient Heptane/EtOAc 85:15->EtOAc) to yield 430 mg (83%) of the title compound as an orange crystalline solid, MS: m/e=217.2, 219.2 (M+H$^+$).

EXAMPLE 2

4-[4-(3-chloro-phenylethynyl)-2-methyl-imidazol-1-yl]-1-methyl-1H-pyridin-2-one

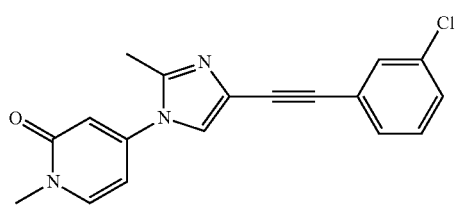

To a solution of 85 mg (0.274 mmol) of 4-[4-(3-chloro-phenylethynyl)-2-methyl-imidazol-1-yl]-1H-pyridin-2-one in 6 ml of DME were added 76 mg (0.55 mmol) of potassium carbonate and 0.034 ml (0.55 mol) of methyl iodide. The suspension was stirred at room temperature for 30 h. The mixture was diluted with 20 ml of ethyl acetate, filtered and concentrated in vaccuo. After purification by flash chromatography on silicagel one obtains 53 mg (0.163 mmol, 60%) of the title compound, as a crystalline yellow solid, MS: m/e=324.2, 326.2 (M+H$^+$).

EXAMPLE 3

4-[4-(3-chloro-phenylethynyl)-2-methyl-imidazol-1-yl]-1-ethyl-1H-pyridin-2-one

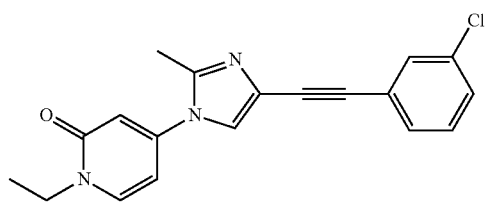

The title compound, orange gum, MS: m/e=338.3, 340.2 (M+H$^+$), was prepared in accordance with the general method of example 2 from 4-[4-(3-chloro-phenylethynyl)-2-methyl-imidazol-1-yl]-1H-pyridin-2-one and ethyl iodide in acetone instead of DME.

EXAMPLE 4

4-[4-(3-chloro-phenylethynyl)-2-methyl-imidazol-1-yl]-1-(2-hydroxy-ethyl)-1H-pyridin-2-one

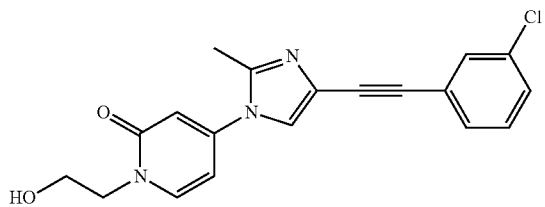

The title compound, orange gum, MS: m/e=354.2, 356.2 (M+H⁺), was prepared in accordance with the general method of example 3 from 4-[4-(3-chloro-phenylethynyl)-2-methyl-imidazol-1-yl]-1H-pyridin-2-one and 2-iodoethanol.

EXAMPLE 5

4-[4-(3-chloro-phenylethynyl)-2-methyl-imidazol-1-yl]-1-(2-methoxy-ethyl)-1H-pyridin-2-one

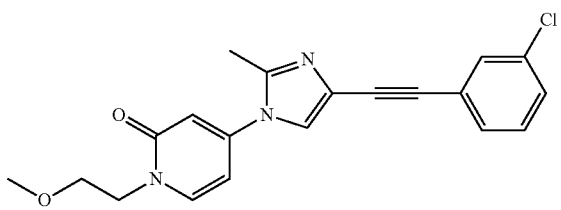

The title compound, light brown solid. MS: m/e=368.1, 370.0 (M+H⁺), was prepared in accordance with the general method of example 3 from 4-[4-(3-chloro-phenylethynyl)-2-methyl-imidazol-1-yl]-1H-pyridin-2-one and 2-bromoethyl-methylether.

EXAMPLE 6

4-[4-(2-chloro-pyridin-4-ylethynyl)-2-methyl-imidazol-1-yl]-1H-pyridin-2-one

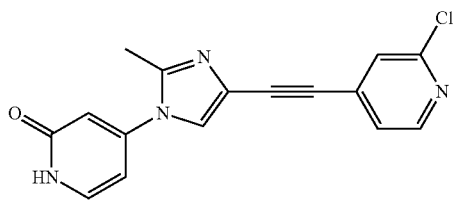

a) The title compound, white crystalline solid, MS: m/e=311.2, 313.2 (M+H⁺), was prepared in accordance with the general method of example 1a by treatment of 2-chloro-4-[4-(2-chloro-pyridin-4-ylethynyl)-2-methyl-imidazol-1-yl]-pyridine with 50% KOH in tert-butanol b) 2-chloro-4-[4-(2-chloro-pyridin-4-ylethynyl)-2-methyl-imidazol-1-yl]-pyridine The title compound, white crystalline solid, MS: m/e=329.2, 331.1 (M+H⁺) was prepared in accordance with the general method of example 1b from 2-chloro-4-(2-methyl-1H-imidazol-4-ylethynyl)-pyridine (CAS: [802905-83-5]) and 2-chloro-4-fluoropyridine.

EXAMPLE 7

4-[4-(2-chloro-pyridin-4-ylethynyl)-2-methyl-imidazol-1-yl]-1-methyl-1H-pyridin-2-one

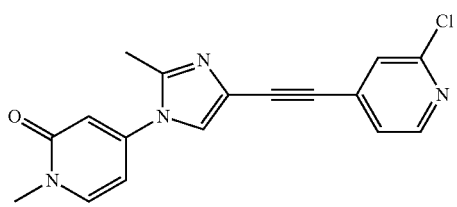

The title compound, white crystalline solid, MS: m/e=325.2, 327.1 (M+H⁺), was prepared in accordance with the general method of example 2 from 4-[4-(2-chloro-pyridin-4-ylethynyl)-2-methyl-imidazol-1-yl]-1H-pyridin-2-one and methyl iodide.

EXAMPLE 8

4-(2-Methyl-4-m-tolylethynyl-imidazol-1-yl)-1H-pyridin-2-one

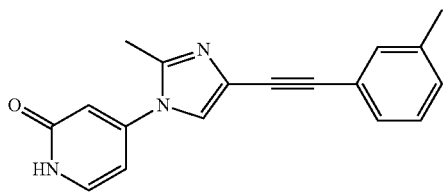

a) The title compound, white solid, MS: m/e=290.1 (M+H⁺), was prepared in accordance with the general method of example 1a from 2-chloro-4-(2-methyl-4-m-tolylethynyl-imidazol-1-yl)-pyridine and KOH in tert-butanol.

b) 2-chloro-4-(2-methyl-4-m-tolylethynyl-imidazol-1-yl)-pyridine

The title compound, light brown solid, MS: m/e=308.2, 310.1 (M+H⁺) was prepared in accordance with the general method of example 1b from 2-Methyl-4-m-tolylethynyl-1H-imidazole and 2-chloro-4-fluoropyridine c) 2-Methyl-4-m-tolylethynyl-1H-imidazole The title compound, orange solid, MS: m/e=197.2 (M+H$^+$) was prepared in accordance with the general method of example 1c from 5-iodo-2-methyl-1H-imidazole and 1-ethynyl-3-methyl-benzene.

EXAMPLE 9

1-Methyl-4-(2-methyl-4-m-tolylethynyl-imidazol-1-yl)-1H-pyridin-2-one

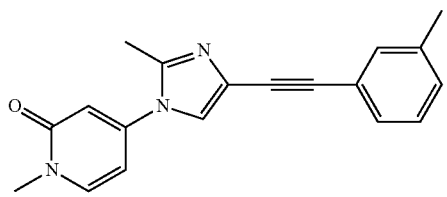

The title compound, light brown solid, MS: m/e=304.2 (M+H$^+$), was prepared in accordance with the general method of example 3 from 4-(2-Methyl-4-m-tolylethynyl-imidazol-1-yl)-1H-pyridin-2-one and methyl iodide.

EXAMPLE 10

1-Ethyl-4-(2-methyl-4-m-tolylethynyl-imidazol-1-yl)-1H-pyridin-2-one

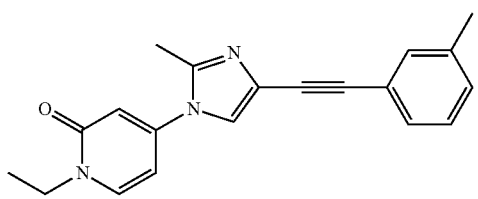

The title compound, light brown solid, MS: m/e=318.2 (M+H$^+$), was prepared in accordance with the general method of example 3 from 4-(2-Methyl-4-m-tolylethynyl-imidazol-1-yl)-1H-pyridin-2-one and ethyl iodide.

EXAMPLE 11

1-(2-Hydroxy-ethyl)-4-(2-methyl-4-m-tolylethynyl-imidazol-1-yl)-1H-pyridin-2-one

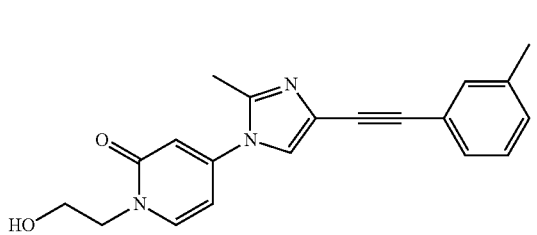

The title compound, light yellow solid, MS: m/e=334.2 (M+H$^+$), was prepared in accordance with the general method of example 3 from 4-(2-Methyl-4-m-tolylethynyl-imidazol-1-yl)-1H-pyridin-2-one and 2-iodoethanol.

EXAMPLE 12

1-(2-Methoxy-ethyl)-4-(2-methyl-4-m-tolylethynyl-imidazol-1-yl)-1H-pyridin-2-one

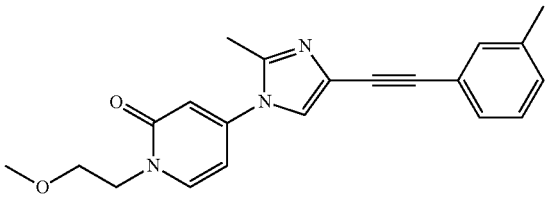

The title compound, colorless resin, MS: m/e=348.3 (M+H$^+$), was prepared in accordance with the general method of example 3 from 4-(2-Methyl-4-m-tolylethynyl-imidazol-1-yl)-1H-pyridin-2-one and 2-bromoethyl-methylether.

EXAMPLE 13

[4-(2-Methyl-4-m-tolylethynyl-imidazol-1-yl)-2-oxo-2H-pyridin-1-yl]-acetic acid ethyl ester

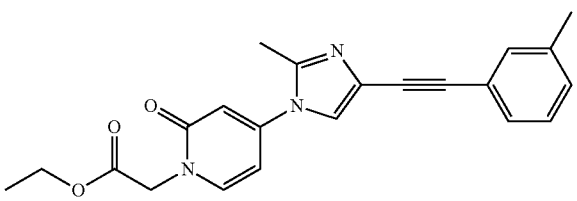

The title compound, brown solid, MS: m/e=376.3 (M+H$^+$), was prepared in accordance with the general method of example 3 from 4-(2-Methyl-4-m-tolylethynyl-imidazol-1-yl)-1H-pyridin-2-one and ethyl bromoacetate.

EXAMPLE 14

6-[4-(3-chloro-phenylethynyl)-2-methyl-imidazol-1-yl]-pyridin-2-ol

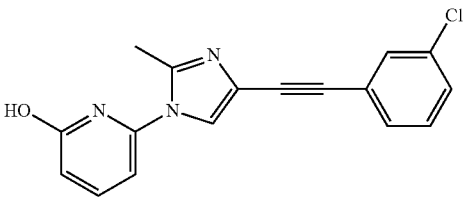

a) The title compound, light yellow solid, MS: m/e=310.1, 312.0 (M+H), was prepared in accordance with the general method of example 1a from 2-[4-(3-chloro-phenylethynyl)-2-methyl-imidazol-1-yl]-6-fluoro-pyridine and KOH in tert-butanol.

b) 2-[4-(3-chloro-phenylethynyl)-2-methyl-imidazol-1-yl]-6-fluoro-pyridine

The title compound, off-white cristalline solid, MS: m/e=312.1, 314.1 (M+H⁺) was prepared in accordance with the general method of example 1b from 4-(3-chloro-phenylethynyl)-2-methyl-1H-imidazole and 2,6-difluoropyridine.

EXAMPLE 15

6-[4-(3-chloro-phenylethynyl)-2-methyl-imidazol-1-yl]-1-methyl-1H-pyridin-2-one

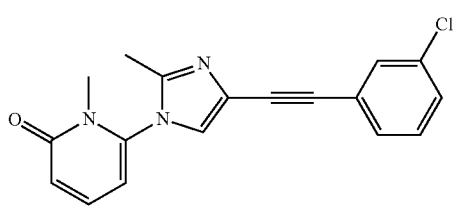

The title compound, off-white cristalline solid, MS: m/e=324.2, 326.1 (M+H), was prepared in accordance with the general method of example 3 from 6-[4-(3-chloro-phenylethynyl)-2-methyl-imidazol-1-yl]-pyridin-2-ol and methyl iodide, along with the O-alkylation product from which it was separated by flash chromatography (gradient: EtOAc to EtOAc/MeOH 95:5).

EXAMPLE 16

6-[4-(3-chloro-phenylethynyl)-2-methyl-imidazol-1-yl]-1H-pyrazin-2-one

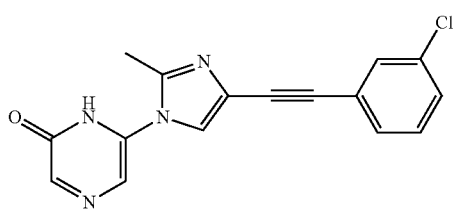

a) A solution of 75 mg (0.214 mmol) 2-Allyloxy-6-[4-(3-chloro-phenylethynyl)-2-methyl imidazol-1-yl]-pyrazine in 5 ml of methylene chloride was degassed with argon. Then 0.052 ml (0.428 mmol) of phenyl silane and 2.5 mg (0.002 mmol) of tetrakis(triphenyl-phosphine)palladium were added and the mixture was stirred for 1 h at room temperature. Then water (1 ml) was added and the mixture was vigourously stirred for 5 min., diluted with 10 ml of methylene chloride and the organic phase was washed with water and brine, dried over magnesium sulfate and concentrated. The obtained solid was triturated with benzene to remove impurities (triphenylphosphine oxide), filtered and dried to yield 30 mg (0.097 mmol, 45%) of the title compound as a white crystalline solid, MS: m/e=311.1, 313.1 (M+H⁺)

b) 2-Allyloxy-6-[4-(3-chloro-phenylethynyl)-2-methyl-imidazol-1-yl]-pyrazine

The title compound, white cristalline solid, MS: m/e=351.2, 353.2 (M+H⁺), was prepared in accordance with the general method of example 1b from 4-(3-chloro-phenylethynyl)-2-methyl-1H-imidazole and 2-Allyloxy-6-chloropyrazine (CAS: [107466-49-9].

EXAMPLE 17

6-[4-(2-chloro-pyridin-4-ylethynyl)-2-methyl-imidazol-1-yl]-pyridin-2-ol

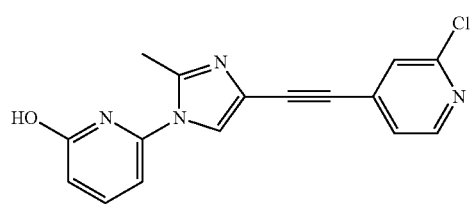

a) The title compound, white cristalline solid, MS: m/e=311.2, 313.2 (M+H⁺), was prepared in accordance with the general method of example 1a from 2-fluoro-6-[4-(2-chloro-pyridin-4-ylethynyl)-2-methyl-imidazol-1-yl]-pyridine and KOH in tert-butanol.

b) 2-fluoro-6-[4-(2-chloro-pyridin-4-ylethynyl)-2-methyl-imidazol-1-yl]-pyridine The title compound, off-white cristalline solid, MS: m/e=313.2, 315.1 (M+H⁺) was prepared in accordance with the general method of example 1b from 2-chloro-4-(2-methyl-1H-imidazol-4-ylethynyl)-pyridine and 2,6-difluoropyridine.

EXAMPLE 18

6-[4-(2-chloro-pyridin-4-ylethynyl)-2-methyl-imidazol-1-yl]-1-methyl-1H-pyridin-2-one

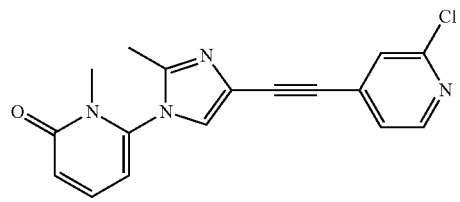

The title compound, yellow cristalline solid, MS: m/e=325.2, 327.1 (M+H⁺), was prepared in accordance with the general method of example 2 from 6-[4-(2-chloro-pyridin-4-ylethynyl)-2-methyl-imidazol-1-yl]-pyridin-2-ol and methyl iodide, along with the O-alkylation product from which it was separated by flash chromatography (gradient: EtOAc to EtOAc/MeOH 95:5).

EXAMPLE 19

6-[4-(2-chloro-pyridin-4-ylethynyl)-2-methyl-imidazol-1-yl]-1H-pyrazin-2-one

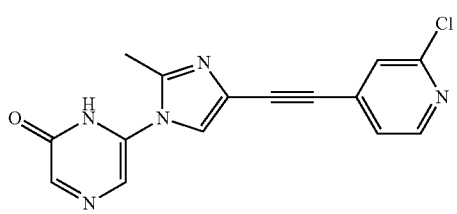

a) The title compound, off-white cristalline solid, MS: m/e=312.0, 314.0 (M+H+), was prepared in accordance with the general method of example 1a from 2-Allyloxy-6-[4-(2-chloro-pyridin-4-ylethynyl)-2-methyl-imidazol-1-yl]-pyrazine.

b) 2-Allyloxy-6-[4-(2-chloro-pyridin-4-ylethynyl)-2-methyl-imidazol-1-yl]-pyrazine The title compound, light yellow viscous oil, MS: m/e=352.2, 354.2 (M+H+), was prepared in accordance with the general method of example 1b from 2-chloro-4-(2-methyl-1H-imidazol-4-ylethynyl)-pyridine (CAS: [802905-83-5]) and 2-Allyloxy-6-chloro-pyrazine (CAS: [107466-49-9].

EXAMPLE 20

6-[4-(2-chloro-pyridin-4-ylethynyl)-2-methyl-imidazol-1-yl]-1-methyl-1H-pyrazin-2-one

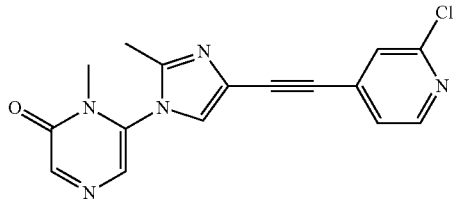

The title compound, yellow cristalline solid, MS: m/e=326.1, 328.2 (M+H+), was prepared in accordance with the general method of example 3 from 6-[4-(2-chloro-pyridin-4-ylethynyl)-2-methyl-imidazol-1-yl]-1H-pyrazin-2-one and methyl iodide, along with the O-alkylation product from which it was separated by flash chromatography (gradient: EtOAc to EtOAc/MeOH 95:5).

EXAMPLE 21

5-[4-(3-chloro-phenylethynyl)-2-methyl-imidazol-1-yl]-2-methyl-2H-pyridazin-3-one

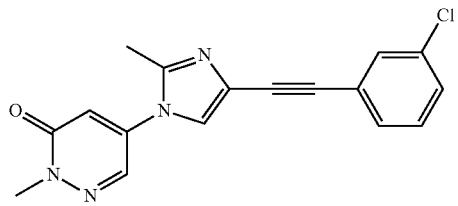

a) A solution of 8 mg bis(triphenyl-phosphine)palladium dichloride in 3 ml of DMF was degassed with argon. Then 52 mg (0.165 mmol) 5-(4-iodo-2-methyl-imidazol-1-yl)-2-methyl-2H-pyridazin-3-one, 1 mg (0.03 mmol) of triphenylphosphine, 0.046 ml (0.33 mmol) triethylamine were added and the mixture was stirred for 5 min at room temperature. Then 1 mg (0.005 mmol) of copper(I) iodide and 0.042 ml (0.33 mmol) of 1-chloro-3-ethynyl-benzene were added and the mixture was stirred for 2 h at 50° C. The mixture was evaporated to dryness in vaccuo, taken up in 5 ml of ethyl acetate. Then ca. 1 g of silicagel was added and the suspension was evaporated to dryness. The silicagel containing adsorbed product was loaded onto a 20 g flash chromatography column. The product was eluted with ethyl acetate. The pure fractions were concentrated to yield 36 mg (0.111 mmol, 67%) of the title compound as a light yellow crystalline solid, MS: m/e=325.2, 327.2 (M+H+).

b) 5-(4-iodo-2-methyl-imidazol-1-yl)-2-methyl-2H-pyridazin-3-one

A solution of 240 mg (0.543 mmol) 5-(4,5-diiodo-2-methyl-imidazol-1-yl)-2-methyl-2H-pyridazin-3-one in 17 ml of dry THF was cooled to −78° C. and 0.41 ml of a 1.6M solution of n-butyllithium (0.65 mmol) in hexane was added. The mixture was stirred for 5 min., quenched by addition of 0.5 ml of methanol and stirred for an additional 10 min at −78° C. Then 2 ml of saturated ammonium chloride solution was added and the mixture was allowed to warm up to room temperature. After standard workup with ethyl acetate/water, the crude material was purified by flash chromatography on silicagel using a 90:10 mixture of ethyl acetate/heptane as eluant to yield 53 mg (0.168 mmol, 31%) of the title compound as a light yellow solid, MS: m/e=316.9 (M+H+).

c) 5-(4,5-diiodo-2-methyl-imidazol-1-yl)-2-methyl-2H-pyridazin-3-one

To a solution of 400 mg (2.10 mmol) of 2-Methyl-5-(2-methyl-imidazol-1-yl)-2H-pyridazin-3-one in 15 ml of DMF was added 2.37 g (10.5 mmol) of N-iodosuccinimide in portions. The mixture was stirred for 24 h at 75° C. After evaporation of the solvent in vaccuo, the residue was taken up in 100 ml of ethyl acetate. After standard workup with ethyl acetate/sodium bicarbonate/sodium bisulfite/brine and drying over magnesium sulfate, the crude material was purified by cristallisation from ethyl acetate/heptane to yield 702 mg (1.588 mmol, 76%) of the title compound as a crystalline light yellow solid, MS: m/e=443.0 (M+H+).

d) 2-Methyl-5-(2-methyl-imidazol-1-yl)-2H-pyridazin-3-one

To a solution of 3.30 g (14.7 mmol) of 4-chloro-2-methyl-5-(2-methyl-imidazol-1-yl)-2H-pyridazin-3-one in 60 ml of ethanol at 50° C. were added 2.44 ml (1.78 g, 17.6 mmol) of triethylamine and 0.312 g of Pd 10%/C. The suspension was stirred under hydrogen atmosphere for 15 h at 50° C. The catalyst was filtered off and washed twice with 10 ml of ethanol. The filtrate was concentrated in vaccuo, and taken up in 50 ml of methylene chloride. The organic phase was washed four times with water, dried and concentrated to yield the title compound (2.30 g, 12.09 mmol, 82%) as a white crystalline solid, MS: m/e=191.2 (M+H+).

e) 4-chloro-2-methyl-5-(2-methyl-imidazol-1-yl)-2H-pyridazin-3-one

A solution of 10.0 g (54.2 mmol) of 4,5-Dichloro-2-methyl-2H-pyridazin-3-one (CAS: [933-76-6]) and 8.90 g (108.4 mmol) of 2-methylimidazole in 50 ml of dioxane was stirred for 16 h at 100° C. The solution was concentrated in vaccuo and the residue was purified by flash chromatography over silicagel using a 95:5 mixture of methylene chloride and methanol as eluant to yield 3.33 g (14.82 mmol, 27%) of the title compound as a white crystalline solid, MS: m/e=225.1, 227.1 (M+H+).

EXAMPLE 22

5-[4-(2-chloro-pyridin-4-ylethynyl)-2-methyl-imidazol-1-yl]-2-methyl-2H-pyridazin-3-one

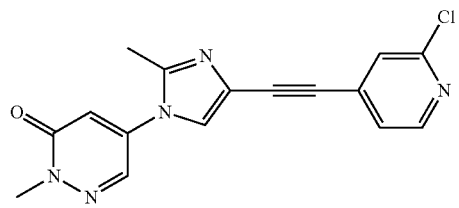

a) The title compound, light brown crystalline solid, MS: m/e=326.2, 328.3 (M+H+), was prepared in accordance with the general method of example 21a from 5-(4-iodo-2-methyl-imidazol-1-yl)-2-methyl-2H-pyridazin-3-one and 2-chloro-4-trimethylsilanyl-ethynyl-pyridine (CAS: [499193-57-6]).

EXAMPLE 23

2-Methyl-5-(2-methyl-4-m-tolylethynyl-imidazol-1-yl)-2H-pyridazin-3-one

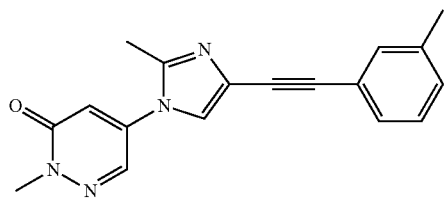

a) The title compound, colorless resin, MS: m/e=305.2 (M+H+), was prepared in accordance with the general method of example 21a from 5-(4-iodo-2-methyl-imidazol-1-yl)-2-methyl-2H-pyridazin-3-one and 1-ethynyl-3-methyl-benzene.

b) 5-(4-iodo-2-methyl-imidazol-1-yl)-2-methyl-2H-pyridazin-3-one

To a solution of 160 mg (1.11 mmol) of 5-chloro-2-methyl-2H-pyridazin-3-one (CAS: [14628-34-3]), 230 mg (1.11 mmol) of 4-iodo-2-methyl-1H-imidazole (CAS: [73746-45-9]), in 3.5 ml of dry DMF were added 721 mg (2.21 mmol) of cesium carbonate. The suspension was stirred for 30 min at 45° C., then for 3 h at 65° C. and allowed to cool. The cristallised product is filtered off, washed with ethyl acetate and dried in vaccuo to yield 250 mg (0.791 mmol, 71%) of the title compound as a crystalline light yellow solid, MS: m/e=316.9 (M+H+).

c) 5-chloro-2-methyl-2H-pyridazin-3-one

A mixture of 1.50 g (10.70 mmol) of 5-methoxy-2-methyl-2H-pyridazin-3-one and 7.8 ml (13.1 g, 85.6 mmol) of phosphorus oxychloride was heated at 110° C. for 2 h. After allowing to cool to room temperature, the mixture was poured into 100 ml of ice/water with vigourous stirring. After neutralization by addition of saturated sodium carbonate solution, the compound was worked up with methylene chloride/water, dried over magnesium sulfate and concentrated in vaccuo. The crude material was purified by flash chromatography on silicagel using a 80:20 mixture of ethyl acetate and heptane as eluant to yield 904 mg (6.25 mmol, 58%) of the title compound as a crystalline white solid, MS: 141.2 (M+H+).

d) 5-Methoxy-2-methyl-2H-pyridazin-3-one

A solution of 3.90 g (22.34 mmol) of 4-chloro-5-methoxy-2-methyl-2H-pyridazin-3-one and 3.74 ml (2.71 g, 26.8 mmol) of triethylamine in 60 ml of ethanol was hydrogenated at atmospheric pressure over 950 mg (0.894 mmol) of 10% palladium on charcoal for 20 h at 55° C. The suspension was filtered hot and the catalyst was washed three times with 10 ml of ethanol. The filtrate was concentrated in vaccuo, and the residue was taken up in 70 ml of methylene chloride, which was washed four times with 20 ml of water, dried over magnesium sulfate and concentrated to yield 2.79 g (19.9 mmol, 89%) of the title compound as a crystalline white solid, MS: 141.2 (M+H+).

e) 4-chloro-5-methoxy-2-methyl-2H-pyridazin-3-one

Sodium metal (613 mg, 26.7 at-g) were dissolved in 35 ml of methanol. To this solution were added 4.15 g (23.18 mmol) of 4,5-dichloro-2-methyl-2H-pyridazin-3-one in four portions over 5 min. After stirring the suspension for 4 h at room temperature, the solution was neutralized by addition of 1 ml sat. ammonium chloride solution and concentrated in vaccuo. The residue was taken up in 100 ml of ethyl acetate, washed twice with water, drie over magnesium sulfate and concentrated in vaccuo to yield 3.94 g (22.6 mmol, 97%) of the title compound as a crystalline white solid, MS: 175.2, 177.0 (M+H+).

EXAMPLE 24

6-[4-(2-chloro-pyridin-4-ylethynyl)-2-methyl-imidazol-1-yl]-3-methyl-3H-pyrimidin-4-one

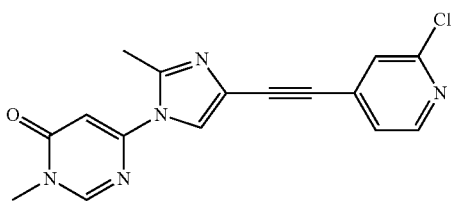

a) To a solution of 50.0 mg (0.160 mmol) of 6-[4-(2-chloro-pyridin-4-ylethynyl)-2-methyl-imidazol-1-yl]-3H-pyrimidin-4-one and 0.020 ml (45.5 mg, 0.321 mmol) of methyl iodide in 10 ml of acetone were added 44 mg (0.321 mmol) of potassium carbonate. The suspension was stirred for 48 at room temperature. The suspension was filtered and the salts were washed with acetone. The filtrate was concentrated in vaccuo. The residue was dissolved in ethyl acetate/methanol, 1 g of silicagel was added and the suspension was concentrated in vaccuo. The silicagel containing adsorbed product was loaded onto a flash chromatography column and eluted with a 90:10 mixture of ethyl acetate and methanol. One obtains 6 mg (0.018 mmol, 11.5%) of the title compound as a crystalline light yellow solid, MS: 326.2, 328.2 (M+H+) separated from the undesired O-alkylation product.

b) 6-[4-(2-chloro-pyridin-4-ylethynyl)-2-methyl-imidazol-1-yl]-3H-pyrimidin-4-one The title compound, white cristalline solid, MS: m/e=MS: 312.0, 314.0 (M+H+), was prepared in accordance with the general method of example 16a by deprotection of 4-allyloxy-6-[4-(2-chloro-pyridin-4-ylethynyl)-2-methyl-imidazol-1-yl]-pyrimidine.

c) 4-allyloxy-6-[4-(2-chloro-pyridin-4-ylethynyl)-2-methyl-imidazol-1-yl]-pyrimidine The title compound, white cristalline solid, MS: m/e=MS: 312.0, 314.0 (M+H+), was prepared in accordance with the general method of example 1b by reaction of 2-chloro-4-(2-methyl-1H-imidazol-4-ylethynyl)-pyridine CAS: [802905-83-5] and 4-allyloxy-6-chloro-pyrimidine.

d) 4-allyloxy-6-chloro-pyrimidine

To a solution of 7.5 g (50.3 mmol) of 4,6-dichloropyrimidine and 3.61 ml (3.07 g, 52.9 mmol) of allyl alcohol in 40 ml of dioxane were added 19.6 g (60.4 mmol) of cesium carbonate. The suspension was stirred for 14 h at 85° C. and then allowed to cool to room temperature. The solution was filtered, and the salts were washed with ethyl acetate. The filtrate was concentrated in vaccuo and purified by flash chromatography on silicagel using ethyl acetate as eluant to yield 4.42 g (25.9 mmol, 51%) of the title compound as a colorless oil.

EXAMPLE 25

4-[4-(3-chloro-phenylethynyl)-2,5-dimethyl-imidazol-1-yl]-1H-pyridin-2-one

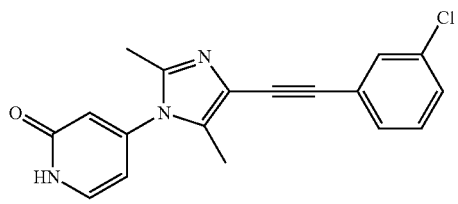

a) The title compound, light brown crystalline solid, MS: m/e=324.2, 326.1 (M+H+), was prepared in accordance with the general method of example 21a from 4-(4-iodo-2,5-dimethyl-imidazol-1-yl)-1H-pyridin-2-one and 1-chloro-3-ethynyl-benzene.

b) 4-(4-iodo-2,5-dimethyl-imidazol-1-yl)-1H-pyridin-2-one

The title compound, white crystalline solid, MS: m/e=315.9 (M+H+), was prepared in accordance with the general method of example 1a from 2-chloro-4-(4-iodo-2,5-dimethyl-imidazol-1-yl)-pyridine and KOH in tert-butanol.

c) 2-chloro-4-(4-iodo-2,5-dimethyl-imidazol-1-yl)-pyridine

The title compound, white crystalline solid, MS: m/e=329.2, 331.1 (M+H$^+$) was prepared in accordance with the general method of example 1b from 4-iodo-2,5-dimethyl-1H-imidazole (CAS: [631897-38-6]) and 2-chloro-4-fluoro-pyridine.

EXAMPLE 26

4-[4-(3-chloro-phenylethynyl)-2,5-dimethyl-imidazol-1-yl]-1-methyl-1H-pyridin-2-one

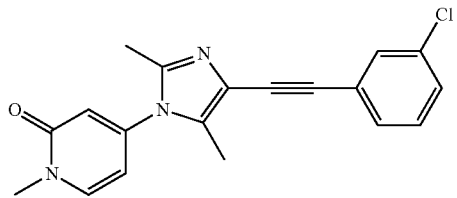

The title compound, white crystalline solid, MS: m/e=338.1, 340.0 (M+H+), was prepared in accordance with the general method of example 3 from 4-[4-(3-chloro-phenylethynyl)-2,5-dimethyl-imidazol-1-yl]-1H-pyridin-2-one and methyl iodide.

EXAMPLE 27

4-[4-(3-chloro-phenylethynyl)-2,5-dimethyl-imidazol-1-yl]-1-ethyl-1H-pyridin-2-one

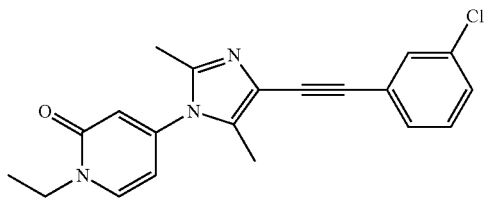

The title compound, white crystalline solid, MS: m/e=352.2, 354.1 (M+H+), was prepared in accordance with the general method of example 3 from 4-[4-(3-chloro-phenylethynyl)-2,5-dimethyl-imidazol-1-yl]-1H-pyridin-2-one and ethyl iodide.

EXAMPLE 28

4-[4-(3-chloro-phenylethynyl)-2,5-dimethyl-imidazol-1-yl]-1-(2-hydroxy-ethyl)-1H-pyridin-2-one

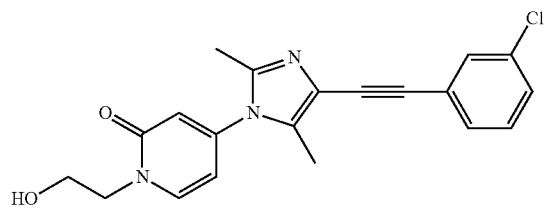

The title compound, white crystalline solid, MS: m/e=368.1, 370.1 (M+H+), was prepared in accordance with the general method of example 3 from 4-[4-(3-chloro-phenylethynyl)-2,5-dimethyl-imidazol-1-yl]-1H-pyridin-2-one and 2-iodoethanol.

EXAMPLE 29

4-[4-(3-chloro-phenylethynyl)-2,5-dimethyl-imidazol-1-yl]-1-(2-methoxy-ethyl)-1H-pyridin-2-one:

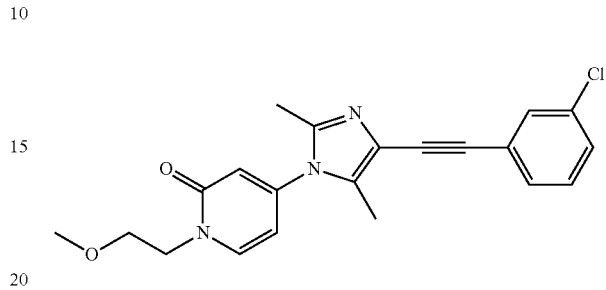

The title compound, white crystalline solid, MS: m/e=382.3, 384.1 (M+H+), was prepared in accordance with the general method of example 3 from 4-[4-(3-chloro-phenylethynyl)-2,5-dimethyl-imidazol-1-yl]-1H-pyridin-2-one and 2-bromoethyl-methylether.

EXAMPLE 30

4-(2,5-dimethyl-4-m-tolylethynyl-imidazol-1-yl)-1H-pyridin-2-one

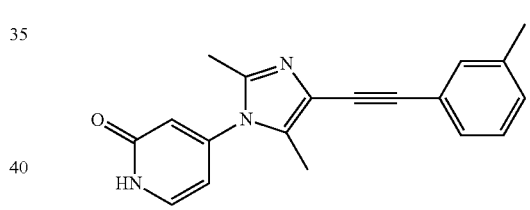

The title compound, light brown solid, MS: m/e=304.1 (M+H+), was prepared in accordance with the general method of example 21a from 4-(4-iodo-2,5-dimethyl-imidazol-1-yl)-1H-pyridin-2-one and 1-Ethynyl-3-methyl-benzene.

EXAMPLE 31

4-[2,5-dimethyl-4-m-tolylethynyl-imidazol-1-yl]-1-methyl-1H-pyridin-2-one

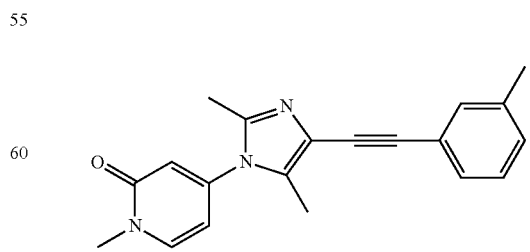

The title compound, brown solid, MS: m/e=318.2 (M+H+), was prepared in accordance with the general method of example 3 from 4-[2,5-dimethyl-4-m-tolylethynyl-imidazol-1-yl]-1H-pyridin-2-one and methyl iodide.

EXAMPLE 32

4-[2,5-dimethyl-4-m-tolylethynyl-imidazol-1-yl]-1-ethyl-1H-pyridin-2-one

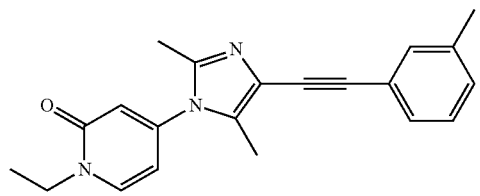

The title compound, light brown solid, MS: m/e=332.2 (M+H+), was prepared in accordance with the general method of example 3 from 4-[2,5-dimethyl-4-m-tolylethynyl-imidazol-1-yl]-1H-pyridin-2-one and ethyl iodide.

EXAMPLE 33

4-[2,5-dimethyl-4-m-tolylethynyl-imidazol-1-yl]-1-(2-hydroxy-ethyl)-1H-pyridin-2-one

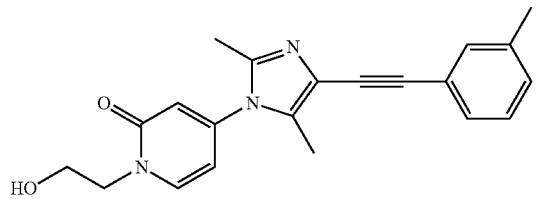

The title compound, light brown solid, MS: m/e=348.2 (M+H+), was prepared in accordance with the general method of example 3 from 4-[2,5-dimethyl-4-m-tolylethynyl-imidazol-1-yl]-1H-pyridin-2-one and 2-iodoethanol.

EXAMPLE 34

4-[2,5-dimethyl-4-m-tolylethynyl-imidazol-1-yl]-1-(2-methoxy-ethyl)-1H-pyridin-2-one

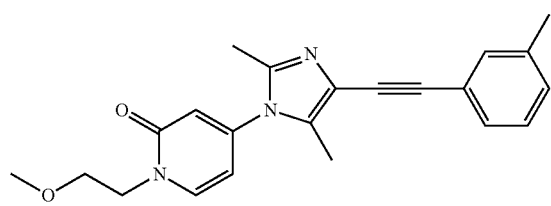

The title compound, light brown solid, MS: m/e=362.3 (M+H+), was prepared in accordance with the general method of example 3 from 4-[2,5-dimethyl-4-m-tolylethynyl-imidazol-1-yl]-1H-pyridin-2-one and 2-bromoethyl-methylether.

EXAMPLE 35

4-[4-(2-chloro-pyridin-4-ylethynyl)-2,5-dimethyl-imidazol-1-yl]-1H-pyridin-2-one

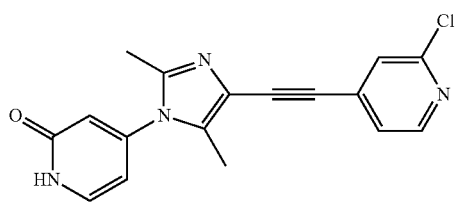

A solution of 47 mg (0.067 mmol) bis(triphenyl-phosphine)palladium dichloride in 4 ml of DMF was degassed with argon. Then 300 mg (0.952 mmol) of 4-(4-iodo-2,5-dimethyl-imidazol-1-yl)-1H-pyridin-2-one, 5 mg (0.019 mmol) of triphenylphosphine, and 0.265 ml (193 mg, 1.90 mmol) of triethylamine were added and the mixture was stirred for 10 min at room temperature. Then 399 mg (1.904 mmol) of 2-chloro-4-trimethylsilanyl-ethynyl-pyridine CAS: [499193-57-6] and 5.4 mg (0.029 mmol) of copper(I) iodide were added and the yellow solution was stirred for another 10 min. The mixture was warmed to 60° C. and 1.43 ml of 1M tetrabutylammonium fluoride solution (1.43 mmol) were added dropwise over a period of 50 min. The dark brown mixture was stirred for 48 h at 50° C., allowed to cool, and was evaporated to dryness in vaccuo. The residue was taken up in 5 ml of ethyl acetate, 3 g of silicagel were added and the suspension was evaporated to dryness. The silicagel containing adsorbed product was loaded onto a 50 g flash chromatography column. The product was eluted with a gradient heptane:ethyl acetate 80:20 to ethyl acetate: methanol 90:10. The pure fractions were concentrated to yield 94 mg (0.289 mmol, 30%) of the title compound as a brown solid, MS: m/e=325.2, 327.1 (M+H+).

EXAMPLE 36

4-[4-(2-chloro-pyridin-4-ylethynyl)-2,5-dimethyl-imidazol-1-yl]-1-methyl-1H-pyridin-2-one

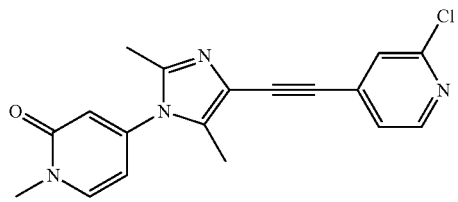

a) The title compound, grey solid, MS: m/e=339.2, 341.1 (M+H+), was prepared in accordance with the general method of example 35 from 4-(4-iodo-2,5-dimethyl-imidazol-1-yl)-1-methyl-1H-pyridin-2-one and 2-chloro-4-trimethylsilanyl-ethynyl-pyridine.

b) 4-(4-iodo-2,5-dimethyl-imidazol-1-yl)-1-methyl-1H-pyridin-2-one

The title compound, white solid, MS: m/e=330.1 (M+H+), was prepared in accordance with the general method of example 3 from 4-(4-iodo-2,5-dimethyl-imidazol-1-yl)-1H-pyridin-2-one and methyl iodide.

EXAMPLE 37

4-[4-(2-chloro-pyridin-4-ylethynyl)-2,5-dimethyl-imidazol-1-yl]-1-ethyl-1H-pyridin-2-one

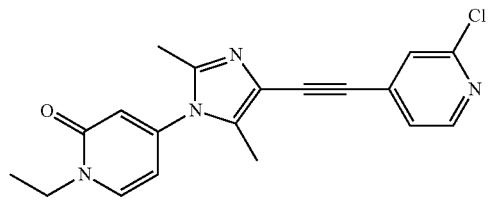

The title compound, light brown solid, MS: m/e=353.3, 355.2 (M+H+), was prepared in accordance with the general method of example 3 from 4-[4-(2-chloro-pyridin-4-ylethynyl)-2,5-dimethyl-imidazol-1-yl]-1H-pyridin-2-one and ethyl iodide.

EXAMPLE 38

4-[4-(2-chloro-pyridin-4-ylethynyl)-2,5-dimethyl-imidazol-1-yl]-1-(2-hydroxy-ethyl)-1H-pyridin-2-one

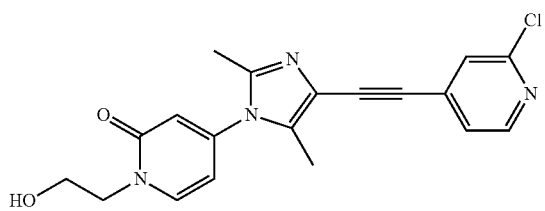

The title compound, orange solid, MS: m/e=369.0, 371.2 (M+H+), was prepared in accordance with the general method of example 3 from 4-[4-(2-chloro-pyridin-4-ylethynyl)-2,5-dimethyl-imidazol-1-yl]-1H-pyridin-2-one and 2-iodoethanol.

EXAMPLE 39

4-[4-(2-chloro-pyridin-4-ylethynyl)-2,5-dimethyl-imidazol-1-yl]-1-(2-methoxy-ethyl)-1H-pyridin-2-one

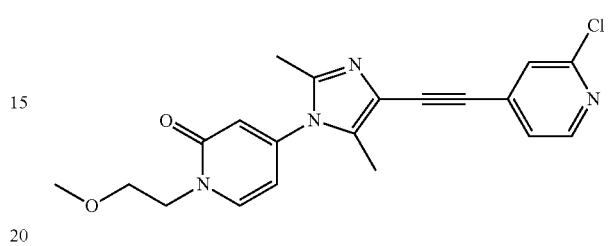

The title compound, light brown solid, MS: m/e=382.3, 384.1 (M+H+), was prepared in accordance with the general method of example 3 from 4-[4-(2-chloro-pyridin-4-ylethynyl)-2,5-dimethyl-imidazol-1-yl]-1H-pyridin-2-one and 2-bromoethyl-methylether.

EXAMPLE 40

4-[4-(3-Methoxy-phenylethynyl)-2,5-dimethyl-imidazol-1-yl]-1H-pyridin-2-one

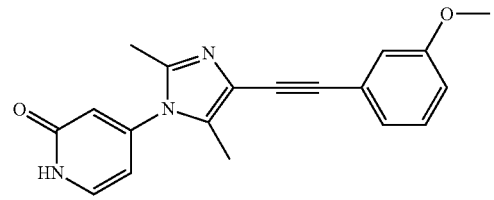

The title compound, light brown solid, MS: m/e=320.1 (M+H+), was prepared in accordance with the general method of example 1c from 4-(4-iodo-2,5-dimethyl-imidazol-1-yl)-1-methyl-1H-pyridin-2-one and 1-Ethynyl-3-methoxy-benzene.

EXAMPLE 41

4-[4-(3-fluoro-phenylethynyl)-2,5-dimethyl-imidazol-1-yl]-1-methyl-1H-pyridin-2-one

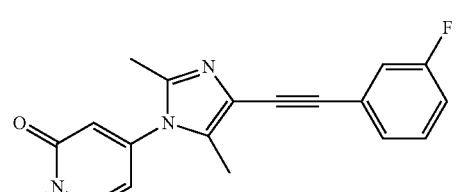

The title compound, brown waxy solid, MS: m/e=322.1 (M+H+), was prepared in accordance with the general method of example 1c from 4-(4-iodo-2,5-dimethyl-imidazol-1-yl)-1-methyl-1H-pyridin-2-one and 1-Ethynyl-3-fluoro-benzene.

EXAMPLE 42

5-[4-(3-chloro-phenylethynyl)-2,5-dimethyl-imidazol-1-yl]-2-methyl-2H-pyridazin-3-one

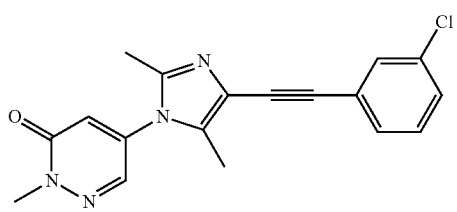

a) The title compound, light brown cristalline solid, MS: m/e=339.2, 341.1 (M+H+), was prepared in accordance with the general method of example 1c from 5-(4-iodo-2,5-dimethyl-imidazol-1-yl)-2-methyl-2H-pyridazin-3-one and 1-chloro-3-ethynyl-benzene.

b) 5-(4-iodo-2,5-dimethyl-imidazol-1-yl)-2-methyl-2H-pyridazin-3-one

The title compound, light yellow cristalline solid, MS: m/e=331.0 (M+H+), was prepared in accordance with the general method of example 23b from 5-chloro-2-methyl-2H-pyridazin-3-one and 4-iodo-2,5-dimethyl-1H-imidazole.

EXAMPLE 43

5-[4-(2-chloro-pyridin-4-ylethynyl)-2,5-dimethyl-imidazol-1-yl]-2-methyl-2H-pyridazin-3-one

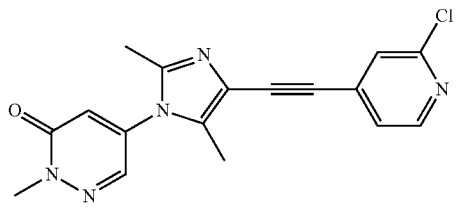

a) The title compound, light brown cristalline solid, MS: m/e=340.2, 342.0 (M+H+), was prepared in accordance with the general method of example 35 from 5-(4-iodo-2,5-dimethyl-imidazol-1-yl)-2-methyl-2H-pyridazin-3-one and 2-chloro-4-trimethylsilanyl-ethynyl-pyridine.

EXAMPLE 44

5-(2,5-dimethyl-4-m-tolylethynyl-imidazol-1-yl)-2-methyl-2H-pyridazin-3-one

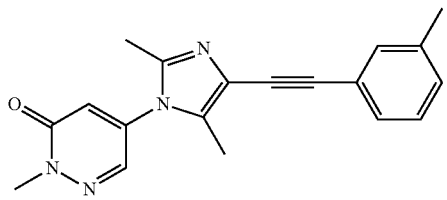

The title compound, light yellow cristalline solid, MS: m/e=319.1 (M+H+), was prepared in accordance with the general method of example 1c from 5-(4-iodo-2,5-dimethyl-imidazol-1-yl)-2-methyl-2H-pyridazin-3-one and 1-ethynyl-3-methyl-benzene.

EXAMPLE 45

6-(2,5-dimethyl-4-m-tolylethynyl-imidazol-1-yl)-3-methyl-3H-pyrimidin-4-one

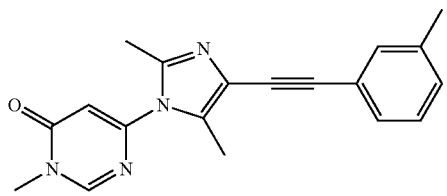

a) The title compound, yellow solid, MS: m/e=319.2 (M+H+), was prepared in accordance with the general method of example 1c from 6-(4-iodo-2,5-dimethyl-imidazol-1-yl)-3-methyl-3H-pyrimidin-4-one and 1-ethynyl-3-methyl-benzene.

b) 6-(4-iodo-2,5-dimethyl-imidazol-1-yl)-3-methyl-3H-pyrimidin-4-one

The title compound, light yellow cristalline solid, MS: m/e=331.0 (M+H+), was prepared in accordance with the general method of example 3 from 6-(4-iodo-2,5-dimethyl-imidazol-1-yl)-3H-pyrimidin-4-one and methyl iodide.

c) 6-(4-iodo-2,5-dimethyl-imidazol-1-yl)-3H-pyrimidin-4-one

The title compound, light yellow crystalline solid, MS: m/e=316.9 (M+H+), was prepared in accordance with the general method of example 1a by treatment of 4-fluoro-6-(4-iodo-2,5-dimethyl-imidazol-1-yl)-pyrimidine with 50% KOH in tert-butanol.

d) 4-fluoro-6-(4-iodo-2,5-dimethyl-imidazol-1-yl)-pyrimidine

The title compound, white cristalline solid, MS: m/e=340.2, 342.1 (M+H+) was prepared in accordance with

EXAMPLE 46

6-[4-(2-chloro-pyridin-4-ylethynyl)-2,5-dimethyl-imidazol-1-yl]-3-methyl-3H-pyrimidin-4-one

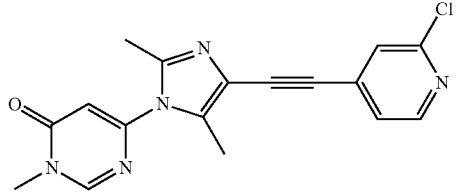

The title compound, light brown cristalline solid, MS: m/e=340.2, 342.1 (M+H+), was prepared in accordance with the general method of example 35 from 6-(4-iodo-2,5-dimethyl-imidazol-1-yl)-3-methyl-3H-pyrimidin-4-one and 2-chloro-4-trimethylsilanyl-ethynyl-pyridine.

EXAMPLE 47

2-[4-(2-methyl-4-m-tolylethynyl-imidazol-1-yl)-2-oxo-2H-pyridin-1-yl]-acetamide

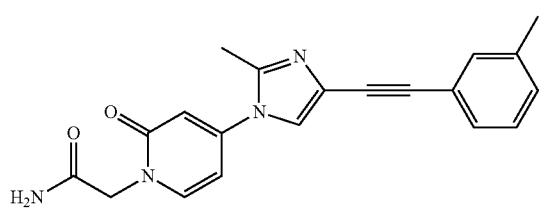

To 2 ml of a 7M solution of ammonia in methanol were added 60 mg (0.16 mmol) of [4-(2-methyl-4-m-tolylethynyl-imidazol-1-yl)-2-oxo-2H-pyridin-1-yl]-acetic acid ethyl ester (Example 13). The reaction vessel was closed and the yellow solution was stirred for 16 h at room temperature. The solution was then evaporated to dryness yielding 45 mg of the title compound as a light brown solid, MS: m/e=347.1 (M+H+).

EXAMPLE 48

N-methyl-2-[4-(2-methyl-4-m-tolylethynyl-imidazol-1-yl)-2-oxo-2H-pyridin-1-yl]-acetamide

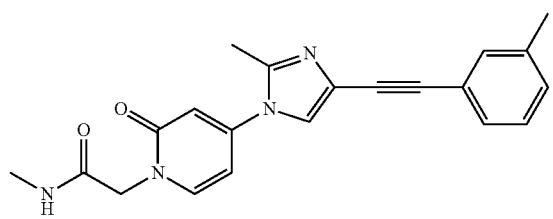

To 2 ml of a 8M solution of methylamine in ethanol were added 67 mg (0.18 mmol) of [4-(2-methyl-4-m-tolylethynyl-imidazol-1-yl)-2-oxo-2H-pyridin-1-yl]-acetic acid ethyl ester (Example 13). The reaction vessel was closed and the yellow solution was stirred for 16 h at room temperature. The solution was then evaporated to dryness yielding 63 mg of the title compound as a light brown solid, MS: m/e=361.2 (M+H+).

EXAMPLE 49

N,N-dimethyl-2-[4-(2-methyl-4-m-tolylethynyl-imidazol-1-yl)-2-oxo-2H-pyridin-1-yl]-acetamide

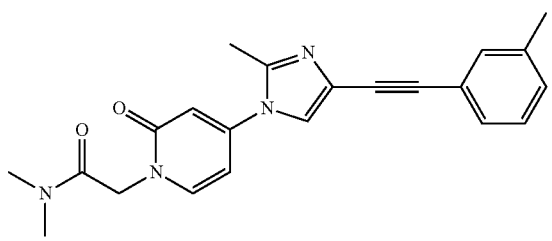

To 2 ml of a 5.6M solution of dimethylamine in ethanol were added 70 mg (0.19 mmol) of [4-(2-methyl-4-m-tolylethynyl-imidazol-1-yl)-2-oxo-2H-pyridin-1-yl]-acetic acid ethyl ester (Example 13). The reaction vessel was closed and the yellow solution was stirred for 2 days at room temperature. The solution was then evaporated to dryness, the residue was triturated with a small amount of ethyl acetate and the product was filtered off, yielding 59 mg of the title compound as a white solid, MS: m/e=375.3 (M+H+).

EXAMPLE 50

N,N-dimethyl-2-[4-(2-methyl-4-m-tolylethynyl-imidazol-1-yl)-2-oxo-2H-pyridin-1-yl]-acetamide

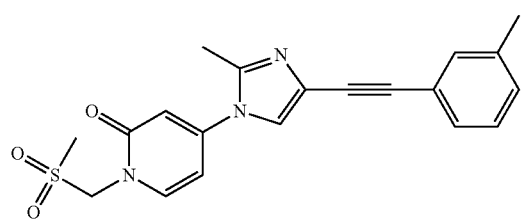

a) To a solution of 15 mg (0.042 mmol) of 1-methylsulfanylmethyl-4-(2-methyl-4-m-tolylethynyl-imidazol-1-yl)-1H-pyridin-2-one in 0.6 ml of methanol were added 53 mg (0.09 mmol) of potassium peroxymonosulfate (Oxone). The mixture was then stirred for 3 h at 40° C. The solution was evaporated to dryness and worked up with methylene chloride/water. The crude material was purified by flash chromatography (SiO2, gradient ethyl acetate to ethyl acetate:methanol 90:10 v/v) to yield 12 mg of the title compound as a white solid, MS: 382.2 (M+H+).

b) 1-methylsulfanylmethyl-4-(2-methyl-4-m-tolylethynyl-imidazol-1-yl)-1H-pyridin-2-one To a solution of 100 mg (0.35 mmol) of 4-(2-Methyl-4-m-tolylethynyl-imidazol-1-yl)-1H-pyridin-2-one in 0.5 ml of dimethylformamide were added 17 mg (0.42 mmol, 1.2 equiv.) of a 60% sodium hydride suspension in mineral oil.

After stirring for 1 h at room temperature, 40 uL (50 mg, 0.52 mmol, 1.5 equiv.) of chloromethyl methylsulfide were added and the suspension was stirred for another 16 h at room temperature. After workup with methylene chloride/water, the crude material was purified by flash chromatography (SiO2, gradient ethyl acetate to ethyl acetate:methanol 90:10 v/v) to yield 32 mg of the title compound as a light yellow solid, MS: 350.2 (M+H+).

EXAMPLE 51

2-ethyl-5-(2-methyl-4-m-tolylethynyl-imidazol-1-yl)-2H-pyridazin-3-one

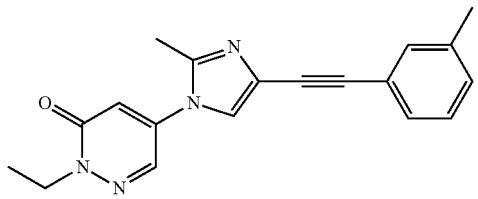

a) The title compound, light brown crystalline solid, MS: m/e=319.1 (M+), was prepared in accordance with the general method of example 21a from 2-ethyl-5-(4-iodo-2-methyl-imidazol-1-yl)-2H-pyridazin-3-one and 1-ethynyl-3-methyl-benzene.

b) 2-ethyl-5-(4-iodo-2-methyl-imidazol-1-yl)-2H-pyridazin-3-one

The title compound, white crystalline solid, MS: m/e=331.0 (M+H+), was prepared in accordance with the general method of example 23b from 5-chloro-2-ethyl-2H-pyridazin-3-one and 4-Iodo-2-methyl-1H-imidazole.

c) 5-chloro-2-ethyl-2H-pyridazin-3-one

The title compound, white crystalline solid, MS: m/e=159.1, 161.1 (M+H+), was prepared in accordance with the general method of example 23c by treatment of 2-ethyl-5-methoxy-2H-pyridazin-3-one with phosphorus oxychloride.

d) 2-ethyl-5-methoxy-2H-pyridazin-3-one

The title compound, white crystalline solid, was prepared in accordance with the general method of example 23d by hydrogenation of 4-chloro-2-ethyl-5-methoxy-2H-pyridazin-3-one.

e) 4-chloro-2-ethyl-5-methoxy-2H-pyridazin-3-one

The title compound, white crystalline solid, was prepared in accordance with the general method of example 23e by treatment of 4,5-dichloro-2-ethyl-2H-pyridazin-3-one with sodium methoxide in methanol.

f) 4,5-dichloro-2-ethyl-2H-pyridazin-3-one

To a suspension of 4.00 g (24.2 mmol) of 4,5-dichloro-2H-pyridazin-3-one (CAS: [932-22-9]) and 6.70 g (48.5 mmol) of potassium carbonate in 40 ml of acetone were added 3.92 ml (7.56 g, 48.5 mmol, 2 eq.) of ethyl iodide. The suspension was stirred for 8 h at 55° C. and allowed to cool to room temperature. The reaction was filtered and the solids were washed twice with acetone. The filtrate was concentrated in vaccuo, taken up in ethyl acetate and the precipitated salts were filtered off. The filtrate was concentrated in vaccuo, taken up in methylene chloride and purified by flash chromatography (SiO2, heptane:ethyl acetate 80:20 v/v) to yield the title compound as a light yellow crystalline solid.

EXAMPLE 52

5-[4-(3-Chloro-phenylethynyl)-2-methyl-imidazol-1-yl]-2-ethyl-2H-pyridazin-3-one

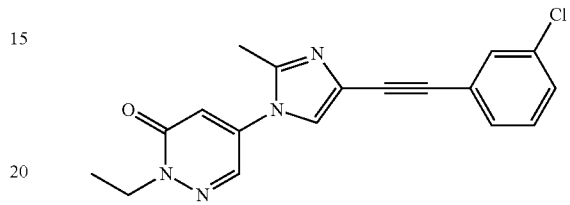

The title compound, light yellow crystalline solid, MS: m/e=339.1, 340.6 (M+H+), was prepared in accordance with the general method of example 21a from 2-ethyl-5-(4-iodo-2-methyl-imidazol-1-yl)-2H-pyridazin-3-one and 1-chloro-3-ethynyl-benzene.

EXAMPLE 53

5-[4-(2-chloro-pyridin-4-ylethynyl)-2-methyl-imidazol-1-yl]-2-ethyl-2H-pyridazin-3-one

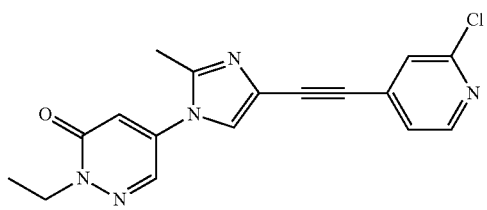

The title compound, light yellow crystalline solid, MS: m/e=339.1, 340.6 (M+H+), was prepared in accordance with the general method of example 35 from 2-ethyl-5-(4-iodo-2-methyl-imidazol-1-yl)-2H-pyridazin-3-one and 2-chloro-4-trimethylsilanylethynyl-pyridine.

EXAMPLE 54

2-(2-methoxy-ethyl)-5-(2-methyl-4-m-tolylethynyl-imidazol-1-yl)-2H-pyridazin-3-one

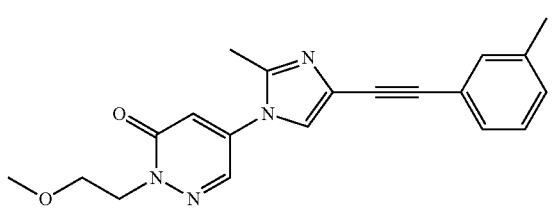

a) The title compound, light yellow viscous oil, MS: m/e=349.4 (M+H+), was prepared in accordance with the general method of example 21a from 2-(2-methoxy-ethyl)-5-(4-iodo-2-methyl-imidazol-1-yl)-2H-pyridazin-3-one and 1-ethynyl-3-methyl-benzene.

b) 2-(2-methoxy-ethyl)-5-(4-iodo-2-methyl-imidazol-1-yl)-2H-pyridazin-3-one

The title compound, light yellow oil, MS: m/e=361.1 (M+H+), was prepared in accordance with the general method of example 23b from 5-chloro-2-(2-methoxy-ethyl)-2H-pyridazin-3-one and 4-Iodo-2-methyl-1H-imidazole.

c) 5-chloro-2-(2-methoxy-ethyl)-2H-pyridazin-3-one

The title compound, light yellow oil, was prepared in accordance with the general method of example 23c by treatment of 2-(2-methoxy-ethyl)-5-methoxy-2H-pyridazin-3-one with phosphorus oxychloride.

d) 2-(2-methoxy-ethyl)-5-methoxy-2H-pyridazin-3-one

The title compound, white crystalline solid, was prepared in accordance with the general method of example 23d by hydrogenation of 4-chloro-2-(2-methoxy-ethyl)-5-methoxy-2H-pyridazin-3-one.

e) 4-chloro-2-(2-methoxy-ethyl)-5-methoxy-2H-pyridazin-3-one

The title compound, white crystalline solid, MS: m/e=219.1, 221.1 (M+H+), was prepared in accordance with the general method of example 23e by treatment of 4,5-dichloro-2-(2-methoxy-ethyl)-2H-pyridazin-3-one with sodium methoxide in methanol.

f) 4,5-dichloro-2-(2-methoxy-ethyl)-2H-pyridazin-3-one

To a suspension of 4.00 g (24.2 mmol) of 4,5-dichloro-2H-pyridazin-3-one and 6.70 g (48.5 mmol) of potassium carbonate in 40 ml of acetone were added 4.55 ml (6.74 g, 48.5 mmol, 2 eq.) of 2-bromoethylmethylether. The suspension was stirred for 24 h at 55° C. Then 1 ml (1.48 g, 10.6 mmol) of 2-bromoethylmethylether were added and the mixture was stirred for another 24 h. The reaction was then allowed to cool to room temperature, the solids were filtered off and washed twice with ethyl acetate. The filtrate was concentrated in vaccuo, taken up in methylene chloride and purified by flash chromatography (SiO2, heptane:ethyl acetate 85:15 v/v) to yield the title compound as a white crystalline solid.

EXAMPLE 55

5-[4-(3-Chloro-phenylethynyl)-2-methyl-imidazol-1-yl]-2-(2-m ethoxy-ethyl)-2H-pyridazin-3-one

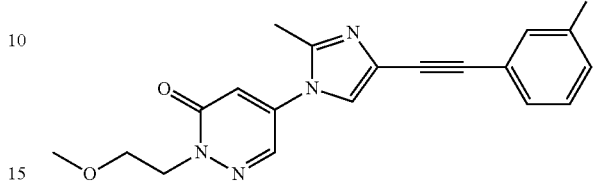

The title compound, yellow crystalline solid, MS: m/e=369.2, 370.9 (M+H+), was prepared in accordance with the general method of example 21a from 5-(4-Iodo-2-methyl-imidazol-1-yl)-2-(2-methoxy-ethyl)-2H-pyridazin-3-one and 1-chloro-3-ethynyl-benzene.

EXAMPLE 56

5-[4-(2-chloro-pyridin-4-ylethynyl)-2-methyl-imidazol-1-yl]-2-ethyl-2H-pyridazin-3-one

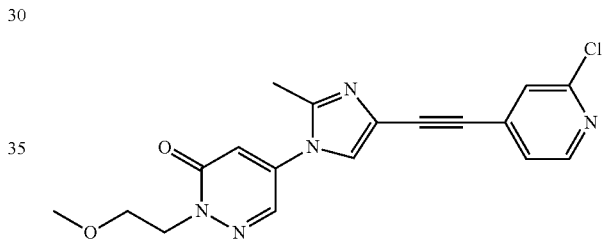

The title compound, white crystalline solid, MS: m/e=370.1, 372.1 (M+H+), was prepared in accordance with the general method of example 35 from 5-(4-Iodo-2-methyl-imidazol-1-yl)-2-(2-methoxy-ethyl)-2H-pyridazin-3-one and 2-chloro-4-trimethylsilanylethynyl-pyridine.

EXAMPLE 57

5-[4-(2-Chloro-pyridin-4-ylethynyl)-2,5-dimethyl-imidazol-1-yl]-2-(2-methoxy-ethyl)-2H-pyridazin-3-one

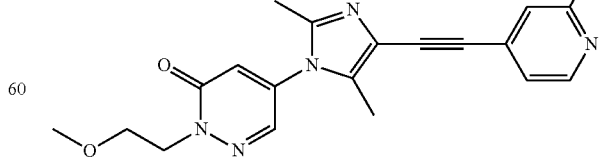

a) The title compound, light brown crystalline solid, MS: m/e=384.2, 386.2 (M+H+), was prepared in accordance with the general method of example 35 from 5-(4-Iodo-2,5-dimethyl-imidazol-1-yl)-2-(2-methoxy-ethyl)-2H-pyridazin-3-one and 2-chloro-4-trimethylsilanylethynyl-pyridine.

b) 5-(4-Iodo-2,5-dimethyl-imidazol-1-yl)-2-(2-methoxy-ethyl)-2H-pyridazin-3-one

The title compound, light yellow waxy solid, MS: m/e=375.2 (M+H+), was prepared in accordance with the general method of example 23b from 5-Chloro-2-(2-methoxy-ethyl)-2H-pyridazin-3-one and 4-iodo-2,5-dimethyl-1H-imidazole.

Preparation of the Pharmaceutical Compositions

EXAMPLE A

Tablets of the following composition are produced in a conventional manner:

|  | mg/Tablet |
| --- | --- |
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in a conventional manner:

|  | mg/Tablet |
| --- | --- |
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

|  | mg/Capsule |
| --- | --- |
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

The invention claimed is:

1. A compound of formula I

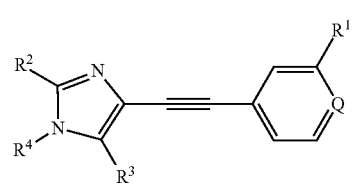

wherein
$R^1$ is halogen, lower alkyl or lower alkoxy;
$R^2$ is lower alkyl, lower hydroxyalkyl or lower alkoxyalkyl;
$R^3$ is hydrogen, lower alkyl, lower hydroxyalkyl or lower alkoxyalkyl;
Q is either —N= or —CH=;
$R^4$ is a group of formula IIa or IIb

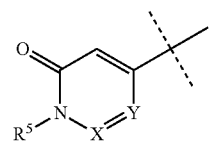

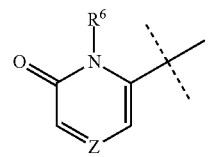

wherein
X, Y and Z are each independently —CH= or —N=, and whereby only one of X or Y is a nitrogen atom;
$R^5$ and $R^6$ are each independently hydrogen, lower alkyl, lower hydroxyalkyl, lower alkoxyalkyl, —(CH$_2$)$_m$—(CO)O-lower alkyl, —(CH$_2$)$_m$—S(O)$_2$-lower alkyl, —(CH$_2$)$_m$—C(O)—NR'R'' and
where m=0-3 and R' and R'' are each independently hydrogen or lower alkyl;
or a pharmaceutically acceptable salt thereof.

2. The compound of claim 1 having formula IA

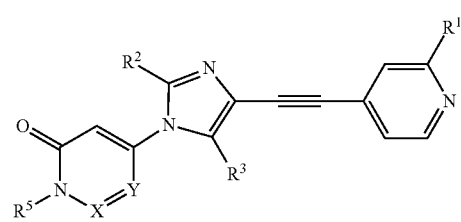

wherein
$R^1$ is halogen, lower alkyl or lower alkoxy;
$R^2$ is lower alkyl, lower hydroxyalkyl or lower alkoxyalkyl;
$R^3$ is hydrogen, lower alkyl, lower hydroxyalkyl or lower alkoxyalkyl;
X, Y and Z are each independently —CH= or —N=, and whereby only one of X or Y is a nitrogen atom;
$R^5$ and $R^6$ are each independently hydrogen, lower alkyl, lower hydroxyalkyl, lower alkoxyalkyl, —(CH$_2$)$_m$—

(CO)O-lower alkyl, —(CH₂)ₘ—S(O)₂-lower alkyl, —(CH₂)ₘ—C(O)—NR'R" and
where m=0-3 and R' and R" are each independently hydrogen or lower alkyl;
or a pharmaceutically acceptable salt thereof.

3. The compound of claim 2, wherein X and Y are —CH═ and R¹ is halogen.

4. The compound of claim 3, selected from the group consisting of
4-[4-(2-chloro-pyridin-4-ylethynyl)-2-methyl-imidazol-1-yl]-1H-pyridin-2-one
4-[4-(2-chloro-pyridin-4-ylethynyl)-2-methyl-imidazol-1-yl]-1-methyl-1H-pyridin-2-one and
4-[4-(2-chloro-pyridin-4-ylethynyl)-2,5-dimethyl-imidazol-1-yl]-1-methyl-1H-pyridin-2-one.

5. The compound of claim 1 having formula IB

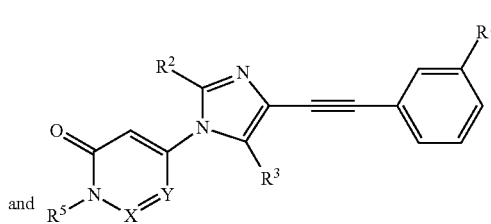

wherein
R¹ is halogen, lower alkyl or lower alkoxy;
R² is lower alkyl, lower hydroxyalkyl or lower alkoxyalkyl;
R³ is hydrogen, lower alkyl, lower hydroxyalkyl or lower alkoxyalkyl;
X, Y and Z are each independently —CH═ or —N═, and whereby only one of X or Y is a nitrogen atom;
R⁵ and R⁶ are each independently hydrogen, lower alkyl, lower hydroxyalkyl, lower alkoxyalkyl, —(CH₂)ₘ—(CO)O-lower alkyl, —(CH₂)ₘ—S(O)₂-lower alkyl, —(CH₂)ₘ—C(O)—NR'R" and
where m=0-3 and R' and R" are each independently hydrogen or lower alkyl;
or a pharmaceutically acceptable salt thereof.

6. The compound of claim 5, wherein X and Y are —CH═ and R¹ is halogen.

7. The compound of claim 6, selected from the group consisting of
4-[4-(3-chloro-phenylethynyl)-2-methyl-imidazol-1-yl]-1H-pyridin-2-one
4-[4-(3-chloro-phenylethynyl)-2-methyl-imidazol-1-yl]-1-methyl-1H-pyridin-2-one
4-[4-(3-chloro-phenylethynyl)-2-methyl-imidazol-1-yl]-1-ethyl-1H-pyridin-2-one
4-[4-(3-chloro-phenylethynyl)-2-methyl-imidazol-1-yl]-1-(2-methoxy-ethyl)-1H-pyridin-2-one
4-[4-(3-chloro-phenylethynyl)-2,5-dimethyl-imidazol-1-yl]-1H-pyridin-2-one
4-[4-(3-chloro-phenylethynyl)-2,5-dimethyl-imidazol-1-yl]-1-methyl-1H-pyridin-2-one
4-[4-(3-chloro-phenylethynyl)-2,5-dimethyl-imidazol-1-yl]-1-ethyl-1H-pyridin-2-one
4-[4-(3-chloro-phenylethynyl)-2,5-dimethyl-imidazol-1-yl]-1-(2-methoxy-ethyl)-1H-pyridin-2-one and
4-[4-(3-fluoro-phenylethynyl)-2,5-dimethyl-imidazol-1-yl]-1-methyl-1H-pyridin-2-one.

8. The compound of claim 5, wherein X and Y are —CH═ and R¹ is lower alkyl.

9. The compound of claim 8, selected from the group consisting of
4-(2-methyl-4-m-tolylethynyl-imidazol-1-yl)-1H-pyridin-2-one
1-methyl-4-(2-methyl-4-m-tolylethynyl-imidazol-1-yl)-1H-pyridin-2-one
1-ethyl-4-(2-methyl-4-m-tolylethynyl-imidazol-1-yl)-1H-pyridin-2-one
1-(2-methoxy-ethyl)-4-(2-methyl-4-m-tolylethynyl-imidazol-1-yl)-1H-pyridin-2-one
[4-(2-methyl-4-m-tolylethynyl-imidazol-1-yl)-2-oxo-2H-pyridin-1-yl]-acetic acid ethyl ester
4-[2,5-dimethyl-4-m-tolylethynyl-imidazol-1-yl]-1-methyl-1H-pyridin-2-one
4-[2,5-dimethyl-4-m-tolylethynyl-imidazol-1-yl]-1-ethyl-1H-pyridin-2-one and
4-[2,5-dimethyl-4-m-tolylethynyl-imidazol-1-yl]-1-(2-methoxy-ethyl)-1H-pyridin-2-one.

10. The compound of claim 5, wherein X is —N═ and Y is —CH═ and R¹ is halogen.

11. The compound of claim 10, selected from the group consisting of
5-[4-(3-chloro-phenylethynyl)-2-methyl-imidazol-1-yl]-2-methyl-2H-pyridazin-3-one
5-[4-(3-chloro-phenylethynyl)-2,5-dimethyl-imidazol-1-yl]-2-methyl-2H-pyridazin-3-one
5-[4-(3-Chloro-phenylethynyl)-2-methyl-imidazol-1-yl]-2-ethyl-2H-pyridazin-3-one and
5-[4-(3-chloro-phenylethynyl)-2-methyl-imidazol-1-yl]-2-(2-methoxy-ethyl-2H-pyridazin-3-one.

12. The compound of claim 5, wherein X is —N═ and Y is —CH═ and R¹ is lower alkyl.

13. The compound of claim 12, selected from the group consisting of
2-Methyl-5-(2-methyl-4-m-tolylethynyl-imidazol-1-yl)-2H-pyridazin-3-one
5-(2,5-dimethyl-4-m-tolylethynyl-imidazol-1-yl)-2-methyl-2H-pyridazin-3-one
2-ethyl-5-(2-methyl-4-m-tolylethynyl-imidazol-1-yl)-2H-pyridazin-3-one and
2-(2-methoxy-ethyl)-5-(2-methyl-4-m-tolylethynyl-imidazol-1-yl)-2H-pyridazin-3-one.

14. The compound of claim 5, wherein X is —CH═ and Y is —N═ and R¹ is lower alkyl.

15. The compound of claim 14, which compound is 6-(2,5-dimethyl-4-m-tolylethynyl-imidazol-1-yl)-3-methyl-3H-pyrimidin-4-one.

16. A compound of claim 1 having formula IC

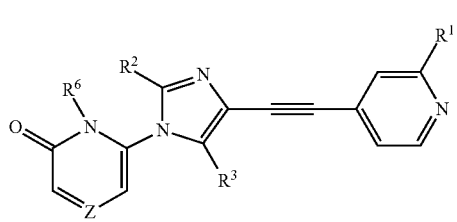

wherein
R¹ is halogen, lower alkyl or lower alkoxy;
R² is lower alkyl, lower hydroxyalkyl or lower alkoxyalkyl;
R³ is hydrogen, lower alkyl, lower hydroxyalkyl or lower alkoxyalkyl;

X, Y and Z are each independently —CH= or —N=, and whereby only one of X or Y is a nitrogen atom;

R$^5$ and R$^6$ are each independently hydrogen, lower alkyl, lower hydroxyalkyl, lower alkoxyalkyl, —(CH$_2$)$_m$—(CO)O-lower alkyl, —(CH$_2$)$_m$—S(O)$_2$-lower alkyl, —(CH$_2$)$_m$—C(O)—NR'R" and where m=0-3 and R' and R" are each independently hydrogen or lower alkyl;

or a pharmaceutically acceptable salt thereof.

17. The compound of claim 16, wherein Z is —CH= and R$^1$ is halogen.

18. The compound of claim 1 having formula ID

ID wherein

R$^1$ is halogen, lower alkyl or lower alkoxy;

R$^2$ is lower alkyl, lower hydroxyalkyl or lower alkoxyalkyl;

R$^3$ is hydrogen, lower alkyl, lower hydroxyalkyl or lower alkoxyalkyl;

X, Y and Z are each independently —CH= or —N=, and whereby only one of X or Y is a nitrogen atom;

R$^5$ and R$^6$ are each independently hydrogen, lower alkyl, lower hydroxyalkyl, lower alkoxyalkyl, —(CH$_2$)$_m$—(CO)O-lower alkyl, —(CH$_2$)$_m$—S(O)$_2$-lower alkyl, —(CH$_2$)$_m$—C(O)—NR'R" and where m=0-3 and R' and R" are each independently hydrogen or lower alkyl;

or a pharmaceutically acceptable salt thereof.

19. The compound of claim 18, wherein Z is —CH= and R$^1$ is halogen.

20. The compound of claim 19, selected from the group consisting of

6-[4-(3-chloro-phenylethynyl)-2-methyl-imidazol-1-yl]-1-methyl-1H-pyridin-2-one.

21. A pharmaceutical composition comprising a therapeutically effective amount of a compound of formula I (I)

wherein

R$^1$ is halogen, lower alkyl or lower alkoxy;

R$^2$ is lower alkyl, lower hydroxyalkyl or lower alkoxyalkyl;

R$^3$ is hydrogen, lower alkyl, lower hydroxyalkyl or lower alkoxyalkyl;

Q is either —N= or —CH=;

R$^4$ is a group of formula IIa or IIb

IIa

IIb wherein

X, Y and Z are each independently —CH= or —N=, and whereby only one of X or Y is a nitrogen atom;

R$^5$ and R$^6$ are each independently hydrogen, lower alkyl, lower hydroxyalkyl, lower alkoxyalkyl, —(CH$_2$)$_m$—(CO)O-lower alkyl, —(CH$_2$)$_m$—S(O)$_2$-lower alkyl, —(CH$_2$)$_m$—C(O)—NR'R" and where m=0-3 and R' and R" are each independently hydrogen or lower alkyl;

or a pharmaceutically acceptable salt thereof and a pharmaceutically acceptable carrier.

* * * * *

UNITED STATES PATENT AND TRADEMARK OFFICE
CERTIFICATE OF CORRECTION

PATENT NO. : 8,334,287 B2  
APPLICATION NO. : 12/833017  
DATED : December 18, 2012  
INVENTOR(S) : George Jaeschke et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 88 days.

Signed and Sealed this
Twenty-first Day of May, 2013

Teresa Stanek Rea
*Acting Director of the United States Patent and Trademark Office*